(12) United States Patent
Maneri et al.

(10) Patent No.: US 10,902,950 B2
(45) Date of Patent: Jan. 26, 2021

(54) COLLABORATIVE HEALTHCARE

(71) Applicant: Accenture Global Services Limited, Dublin (IE)

(72) Inventors: Erin Maneri, San Jose, CA (US); Pramila Mullan, Los Gatos, CA (US); Brad H. Ruderman, San Francisco, CA (US); Alice Tsing, Arcadia, CA (US); Jitendra Kavathekar, Cupertino, CA (US); Dadong Wan, San Jose, CA (US)

(73) Assignee: ACCENTURE GLOBAL SERVICES LIMITED, Dublin (IE)

( * ) Notice: Subject to any disclaimer, the term of this patent is extended or adjusted under 35 U.S.C. 154(b) by 357 days.

(21) Appl. No.: 14/012,658

(22) Filed: Aug. 28, 2013

(65) Prior Publication Data

US 2014/0303988 A1    Oct. 9, 2014

Related U.S. Application Data

(60) Provisional application No. 61/810,113, filed on Apr. 9, 2013.

(51) Int. Cl.
| | |
|---|---|
| *G16H 50/20* | (2018.01) |
| *G16H 50/30* | (2018.01) |
| *G16H 15/00* | (2018.01) |
| *G16H 20/10* | (2018.01) |

(52) U.S. Cl.
CPC ............ *G16H 50/20* (2018.01); *G16H 15/00* (2018.01); *G16H 20/10* (2018.01); *G16H 50/30* (2018.01)

(58) Field of Classification Search
CPC ........ G16H 50/20; G16H 50/30; G16H 15/00; G16H 20/10

USPC ................ 705/2, 3; 607/40; 707/104; 435/7
See application file for complete search history.

(56) References Cited

U.S. PATENT DOCUMENTS

| | | | | |
|---|---|---|---|---|
| 8,224,667 | B1 * | 7/2012 | Miller et al. | ...................... 705/2 |
| 8,285,487 | B2 * | 10/2012 | Bergstrom | ........... A61B 5/0002 |
| | | | | 436/95 |
| 2002/0010597 | A1 * | 1/2002 | Mayer | ................... G06F 19/328 |
| | | | | 705/2 |
| 2003/0152607 | A1 * | 8/2003 | Mault | ................. G06F 19/3475 |
| | | | | 424/439 |
| 2004/0249421 | A1 * | 12/2004 | Harel et al. | ..................... 607/40 |

(Continued)

OTHER PUBLICATIONS

"Patent Examination Report No. 1" on Australia Patent Application No. 2014201974, dated Jul. 11, 2014, IP Australia, 5 pages.

*Primary Examiner* — Jonathan Durant
(74) *Attorney, Agent, or Firm* — Mannava & Kang, P.C.

(57) ABSTRACT

According to an example, collaborative healthcare may include retrieving healthcare data for a patient from at least one data source, and generating a plurality of distinct healthcare programs for the patient based on the healthcare data. Collaborative healthcare may further include reconciling the plurality of distinct healthcare programs to generate a universal patient healthcare plan for the patient. The universal patient healthcare plan may include a universal view of the overall healthcare for the patient and healthcare provider-specific views for the patient. The reconciling may include detecting conflicts for predetermined components of the healthcare programs, and in response to the detection of the conflicts, eliminating errors related to the detected conflicts.

20 Claims, 35 Drawing Sheets

(56) References Cited

U.S. PATENT DOCUMENTS

| | | |
|---|---|---|
| 2006/0129435 A1* | 6/2006 | Smitherman et al. ............ 705/3 |
| 2007/0218519 A1* | 9/2007 | Urdea et al. ................. 435/7.92 |
| 2008/0201174 A1* | 8/2008 | Ramasubramanian ..................... G06F 19/3456 705/3 |
| 2009/0119337 A1* | 5/2009 | Biedermann .............. 707/104.1 |
| 2009/0281826 A1* | 11/2009 | Zak ....................... G06F 19/327 705/2 |
| 2009/0319295 A1* | 12/2009 | Kass-Hout ......... G06Q 10/1095 705/2 |
| 2010/0228570 A1 | 9/2010 | McGuigan et al. |
| 2010/0293007 A1 | 11/2010 | Schoenberg |
| 2010/0332142 A1* | 12/2010 | Shadforth .......... A61B 5/14532 702/19 |
| 2011/0093295 A1* | 4/2011 | Mankad et al. .................. 705/3 |
| 2011/0112865 A1 | 5/2011 | Ying et al. |
| 2012/0290322 A1 | 11/2012 | Bergman et al. |
| 2013/0124226 A1 | 5/2013 | Gedala |

* cited by examiner

| | | | |
|---|---|---|---|
| Rx: Metformin | 1000mg (2x 500mg/day) | | 850mg (1x/day) |
| Rx: Aspirin | | 100mg | |
| Rx: Tylenol 3 | | PRN | |
| Vital: BP | 2x/day | | 1x/day |
| Vital: HbA1c | | once per week | |
| Appt: | X | C N | R U S | U |
| Life: Diet | no carbs | <= 40mg carbs/day | |
| Life: Exercise | 350 cal/day | | 400 cal/day |

Pre-Diabetes

| Trigger | Action (Alert, Appointment, Referral and/or Suggested Change to Care Plan) |
|---|---|
| Metformin Rx not picked up:<br>1. After 1 week<br>2. After 2 weeks | Recommend a cheaper Rx if Metformin too expensive<br>1. Email patient to remind them to pick it up<br>2. Email the provider that patient has not picked up |
| Appointment approaching | Remind patient of upcoming appointment |
| Blood Pressure reading not recorded within<br>1. 1 hour of when its supposed to be taken<br>2. 2 hours of when its supposed to be taken | 3. Text patient and remind them to measure<br>4. Text primary caregiver and have them remind patient |
| Any vital reading out of bounds 3 times consecutively | • Email the care team<br>• Schedule an appointment with PCP<br>• Recommend provider to decrease allotted daily carbs |
| HbA1c out of bounds by<br>1. <= 10% AND at carbs at beginning<br>2. > 10% | 3. Alert provider<br>4. Refer patient to a diabetes specialist |

FIG. 11

| BMI | | |
|---|---|---|
| Definition | Range | % inc/dec |
| Underweight | < 18.5 | ±15% |
| Normal | 18.5-24.9 | ±15% |
| Overweight | 25-29.9 | ±15% |
| Obesity | 30.0-39.9 | ±15% |
| Morbidly Obese | >40.0 | ±15% |

FIG. 21

| HDL | | |
|---|---|---|
| Definition | Range | % Weight Assigned |
| Poor | < 1 | 100% |
| Borderline Low | 1 - 1.5 | 50% |
| Best | ≥ 1.6 | 0% |

| Triglyceride | | |
|---|---|---|
| Definition | Range | % Weight Assigned |
| Normal | ≤ 1.7 | 0% |
| Borderline High | 1.8 - 2.2 | 50% |
| High | 2.3 - 5.6 | 80% |
| Very High | ≥ 5.7 | 100% |

| LDL | | |
|---|---|---|
| Definition | Range | % Weight Assigned |
| Optimal | < 2.59 | 0% |
| Near Optimal | 2.59 - 3.34 | 10% |
| Borderline High | 3.35 - 4.12 | 50% |
| High | 4.13 - 4.9 | 70% |
| Very High | > 4.9 | 100% |

FIG. 26

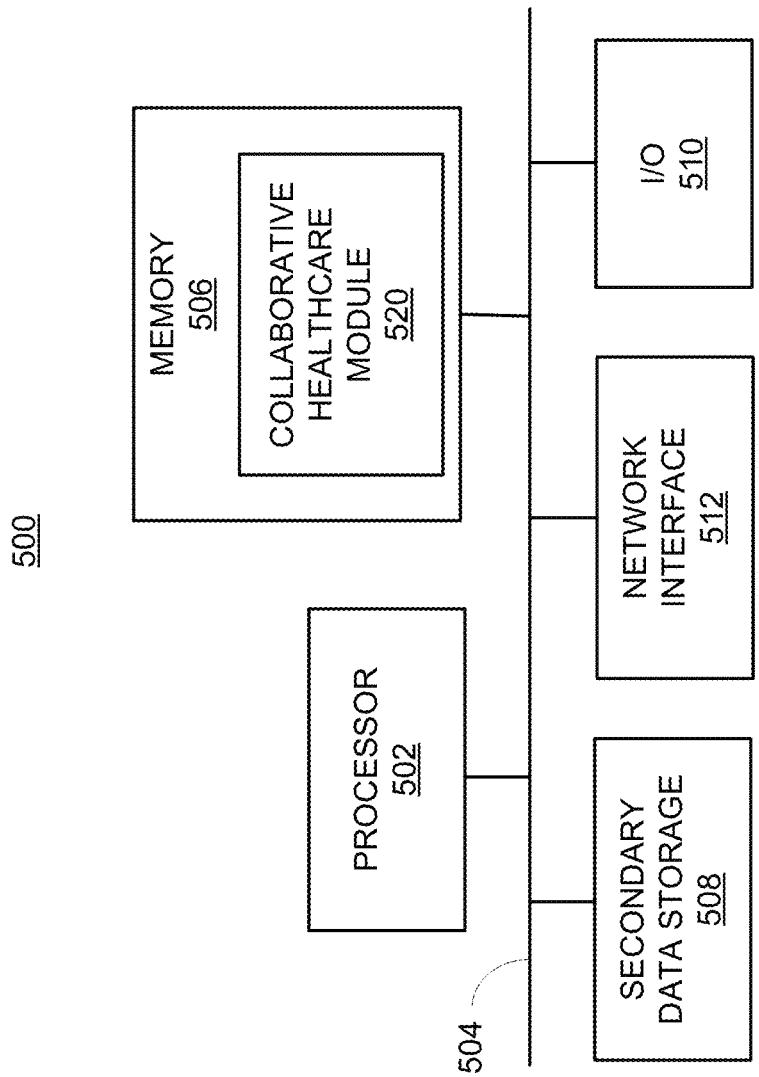

US 10,902,950 B2

COLLABORATIVE HEALTHCARE

CROSS-REFERENCE TO RELATED APPLICATION(S)

This application claims the benefit of provisional patent application U.S. Ser. No. 61/810,113, filed Apr. 9, 2013, which is expressly incorporated herein by reference.

BACKGROUND

Healthcare management typically includes different types of programs that may be involved in a patient's healthcare. For example, a patient may be involved in an allergy program with a physician that specializes in allergy care. The patient may be involved in a pre-diabetes program with another physician that specializes in diabetic care. Similarly, the patient may be involved in a variety of healthcare programs with other physicians of related specialties. The physicians specializing in such diverse fields of healthcare may review available copies of a patient's health records before treating the patient.

BRIEF DESCRIPTION OF DRAWINGS

Features of the present disclosure are illustrated by way of examples shown in the following figures. In the following figures, like numerals indicate like elements, in which:

FIG. 10 illustrates a UI display for a pre-diabetes program for the collaborative healthcare system, according to an example of the present disclosure;

FIG. 11 illustrates triggers and actions for the pre-diabetes program of FIG. 10, according to an example of the present disclosure;

FIG. 21 illustrates a body mass index (BMI) table, according to an example of the present disclosure;

FIG. 26 illustrates patient vitals for cholesterol, according to an example of the present disclosure;

FIG. 35 illustrates a computer system, according to an example of the present disclosure.

DETAILED DESCRIPTION

Figure 1:
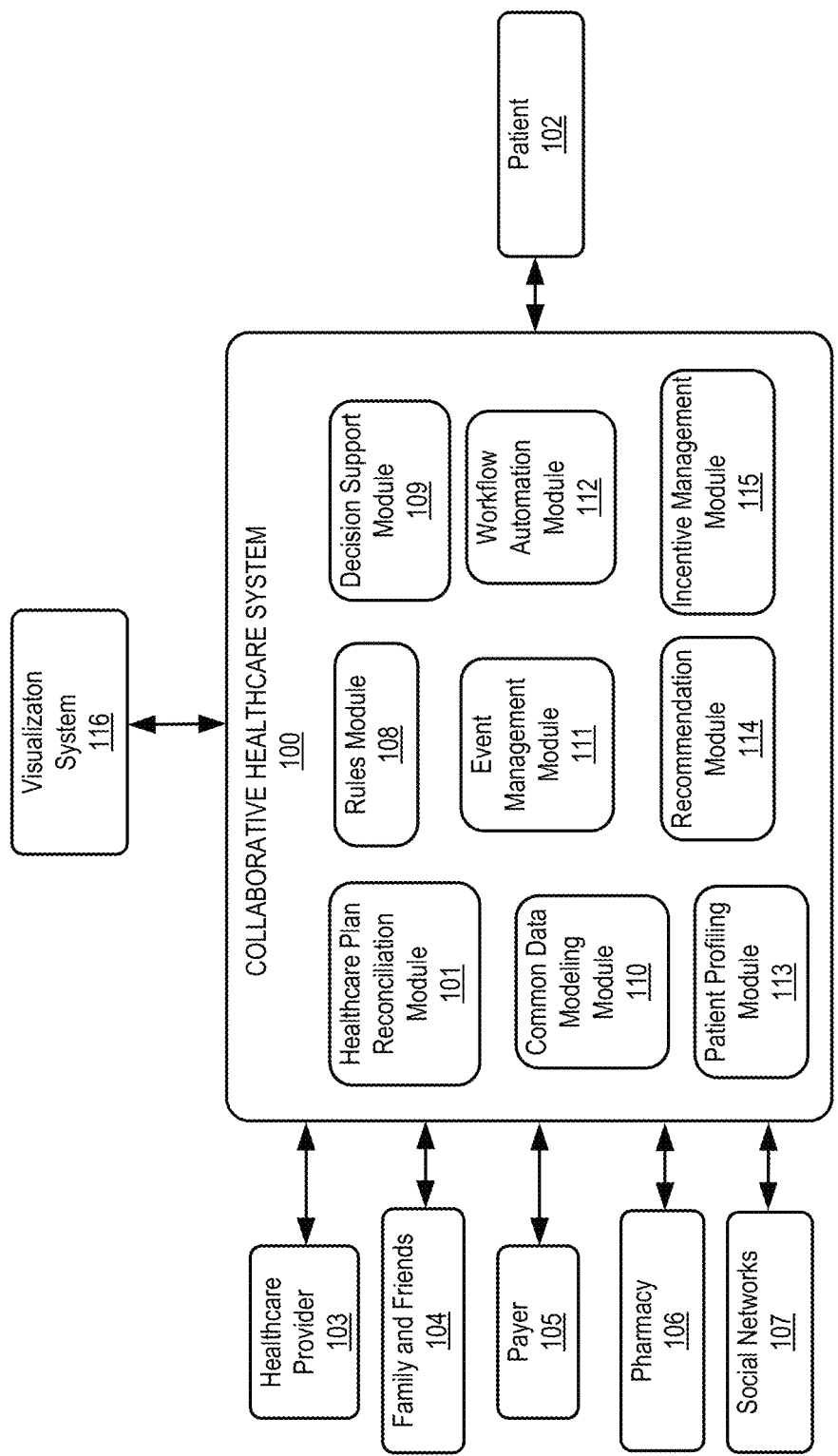
FIG. 1 illustrates an architecture of a collaborative healthcare system, according to an example of the present disclosure.

For simplicity and illustrative purposes, the present disclosure is described by referring mainly to examples. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on.

A collaborative healthcare system, a method for collaborative healthcare, and a non-transitory computer readable medium having stored thereon a computer executable program to provide collaborative healthcare, are disclosed herein and may generally provide automated reconciliation and decision support to manage a patient's universal healthcare plan. The collaborative healthcare disclosed herein may use live data feeds, for example, from health information exchanges and biometric devices, to automatically make healthcare recommendations to healthcare providers based on business rules. The collaborative healthcare disclosed herein may facilitate collaboration between healthcare providers to reconcile differences in a patient's overall healthcare. A patient may be provided with a universal view of the patient's overall healthcare based on automatic reconciliation of a plurality of healthcare programs that form a patient's healthcare plan. Different healthcare providers (e.g., doctors) may be provided with the universal view of the patient's overall healthcare, and may be further provided with healthcare provider-specific views (e.g., healthcare program views) of the patient's healthcare based on automatic reconciliation of the plurality of healthcare programs that form the patient's healthcare plan. The collaborative healthcare disclosed herein may thus provide a bridge between clinical and behavioral modifications through a holistic prescriptive healthcare plan, and through recommendations and incentives. The collaborative healthcare disclosed herein may further provide feedback through monitoring and recommendations, for example, for changes to a healthcare program and/or a healthcare plan.

With respect to reconciliation of healthcare programs that form a patient's healthcare plan, a healthcare plan reconciliation module of the collaborative healthcare system may detect conflicts, for example, between vitals, medications, lifestyle, appointments, and business rule components of a patient's healthcare programs. A patient's healthcare team (e.g., healthcare providers and care givers) may be provided with insight into the health requirements requested by individual healthcare providers. The healthcare plan reconciliation module may eliminate any errors related to a patient's healthcare by deciphering information silos related to individual healthcare programs and healthcare providers. The healthcare plan reconciliation module may provide access to a historical view of a patient's healthcare plan, for example, as designed, as reconciled, and as the healthcare plan changes over time. The changes in the healthcare plan may include modifications to original healthcare programs. The historical view of a patient's healthcare plan may also include user and/or system generated commentary on the rationale for any changes. The healthcare plan reconciliation module may automatically connect healthcare providers associated with conflicting healthcare programs in real-time. If healthcare providers are unavailable for such real-time connections, other techniques, such as e-mails, texts, etc., may be used to inform the healthcare providers to resolve conflict.

With respect to decision support, a decision support module of the collaborative healthcare system may provide for the configuration of individual healthcare programs such that the healthcare programs react to events in the data with alerts, and automatically scheduled appointments. Further, the decision support module may provide suggested changes to individual healthcare programs. A user interface (UI) may allow healthcare providers to configure a rules module to react to events, and provide for the creation of a library of templated healthcare programs. Examples of suggested changes to a healthcare program may include an increase in biometric measurement frequency, decrease in calorie consumption in a diet, etc. Suggestions may be informed based on a patient's preferences. For example, if a patient's profile data indicates that they should lose weight, and they have a preference for weightlifting over cardiovascular exercise, the decision support module may recommend to the healthcare provider that the patient perform, for example, twenty repetitions of three different muscle groups for two sets, three times a week to meet an overall goal of burning 400 calories. The decision support module may operate on data feeds from a patient's personal health records, as well as any third-party data about a patient's behavior (e.g., the sentiment of the patient's TWITTER feeds, which would be an indicator for the patient's mood, or the mention of a jog on the patient's FACEBOOK post).

A visualization system may be provided for operation in conjunction with the collaborative healthcare system or as a component (e.g., a visualization module) thereof. The visualization system may include templated infographics to present all data collected about a patient in context. A common axis may be shared amongst feeds to provide ad-hoc discovery of how signals are interrelated. Common measurements may be synthesized on an individual axis independent of source (e.g., weight measurements from a home scale may be plotted on a same signal as weight measured in a doctor's office, with indicators for the source of the data). Individual data feeds may be combined with a custom process to indicate overall patient health.

The collaborative healthcare disclosed herein may thus provide for reconciliation of multiple healthcare programs from multiple healthcare providers (and their associated rules) into a single healthcare plan to allow all members of a healthcare team to see their patient's full treatment regimen. The reconciliation may also prevent conflicts between different healthcare programs, for example, between medications, vitals, appointments, diet and exercise, and rules for different healthcare programs to thus eliminate any confusion as to what a patient should be doing with respect to their healthcare.

The collaborative healthcare disclosed herein may also provide for access to historic views of healthcare programs, such that the collaborative healthcare system is fully-auditable to versions of healthcare programs as originally designed by a physician, post-reconciliation versions, or in process versions. Templates of common healthcare programs may be included, for example, to build a library of reusable healthcare programs that may use such templates to generate modified healthcare programs. Healthcare programs may be saved as proposals before implementation into an overall healthcare plan, for example, to save session information while confirming or researching healthcare programs that are to be generated. Healthcare programs that are already in a healthcare plan may be modified (per reconciliation) to accommodate changes to the healthcare plan that did not exist upon initial creation of the healthcare plan. Permissions may be set such that access to edit healthcare programs is limited to healthcare providers that are owners of the healthcare programs.

The collaborative healthcare system may include a rules module, for example, to create complex rules logic. The rules module may further trigger alerts to implement and/or propose changes to the healthcare plan, for example, to provide a physician with recommendations on how the healthcare plan may be modified to address problematic outcomes. The rules may also be displayed in a readily understandable language for use, for example, by patients and healthcare providers.

For the collaborative healthcare disclosed herein, when the healthcare plan differs from component healthcare programs thereof, comments explaining changes may be saved in source healthcare programs. The collaborative healthcare disclosed herein may also provide for the retention of all historical changes to the status of appointments, a snapshot of a healthcare plan at any given point in time, and display of historic status changes for appointments, for example, at any point in time (e.g., Ordered→scheduled→no shows→reschedules→cancellations (initiated by patient)→completed). The collaborative healthcare system may also unify a healthcare plan when conflicts arise amongst healthcare programs thereof.

According to an example, a method for collaborative healthcare may include retrieving healthcare data for a patient from at least one data source, and generating a plurality of distinct healthcare programs for the patient based on the healthcare data. The method for collaborative healthcare disclosed herein may further include reconciling the plurality of distinct healthcare programs to generate a universal patient healthcare plan for the patient. The universal patient healthcare plan may include a universal view of the overall healthcare for the patient and healthcare provider-specific views for the patient. The reconciling may include detecting conflicts for predetermined components of the healthcare programs, and in response to the detection of the conflicts, eliminating errors related to the detected conflicts.

According to an example, a collaborative healthcare system may include a memory storing machine readable instructions to receive a plurality of distinct healthcare programs for a patient, and reconcile the plurality of distinct healthcare programs to generate a universal patient healthcare plan for the patient. The universal patient healthcare plan may include a universal view of the overall healthcare for the patient and healthcare provider-specific views for the patient. With respect to reconciling, the machine readable instructions may further detect conflicts for predetermined components of the healthcare programs, and in response to the detection of the conflicts, eliminate errors related to the detected conflicts. The collaborative healthcare system disclosed herein may further include a processor to implement the machine readable instructions.

The collaborative healthcare system, the method for collaborative healthcare, and the non-transitory computer readable medium having stored thereon a computer executable program to provide collaborative healthcare disclosed herein provide a technical solution to the technical problem of collaborative healthcare. In many instances, a patient may be involved in a variety of healthcare programs with different physicians of related specialties. The physicians specializing in such diverse fields of healthcare may review available copies of a patient's health records before treating the patient. The collaborative healthcare disclosed herein provides a technical solution of reconciling a plurality of distinct healthcare programs to generate a universal patient healthcare plan for a patient. The universal patient healthcare plan may include a universal view of the overall healthcare for the patient and healthcare provider-specific views for the patient. The reconciling may include detecting conflicts for predetermined components of the healthcare programs, and in response to the detection of the conflicts, eliminating errors related to the detected conflicts. The collaborative healthcare disclosed herein may also provide a technical solution of determining patient preferences related to the predetermined components, and recommending changes to the healthcare programs based on the patient preferences and the detection of conflicts. The changes to the healthcare programs may be based on social network website data related to behavior of the patient. The collaborative healthcare disclosed herein may further provide a technical solution of monitoring the universal patient healthcare plan to detect a health event related to the patient, and in response to the detection of the health event, generating an alert to the patient related to the health event, a workflow change related to a treatment of the patient, a recommendation to a healthcare provider related to the health event, and an incentive to the patient related to the health event to facilitate the treatment of the patient. The collaborative healthcare disclosed herein may further provide a technical solution of generating a diabetes risk healthcare program for the patient based on the healthcare data, and determining a diabetes risk score for the diabetes risk healthcare program. Determining the diabetes risk score for the diabetes risk healthcare program may include determining a base diabetes score, a patient vitals component, a patient behavioral component, a hospital visit component, and an unfilled medications component for the diabetes risk score.

FIG. 1 illustrates an architecture of a collaborative healthcare system 100, according to an example of the present disclosure. Referring to FIG. 1, the system 100 is depicted as including a healthcare plan reconciliation module 101 to detect conflicts, for example, between vitals, medications, lifestyle, appointments, and business rule components of a patient's healthcare programs, for example, for a patient 102. The system 100 may receive and/or transmit data to a healthcare provider 103, family and friends 104 of the patient 102, a payer 105, a pharmacy 106, and social networks 107. The system 100 may similarly receive and/or transmit data to a plurality of healthcare providers 103, family and friends 104 of patients 102, payers 105, pharmacies 106, and social networks 107. The business rule components may be stored and manipulated by a rules module 108. A decision support module 109 may provide for the configuration of individual healthcare programs, for example, such that the healthcare programs react to events in the data with alerts. A common data modeling module 110 may model common data related, for example, to a healthcare plan and a healthcare team. An event management module 111 may process events (e.g., health events) related, for example, to patient vitals, medications, appointments, etc. A workflow automation module 112 may provide, for example, automatic appointment scheduling and other types of alerts based on health events. A patient profiling module 113 may receive and pre-process patient profile information for use by the decision support module 109 and a recommendation module 114 for the patient 102. The recommendation module 114 may provide recommendations based on health events, for example, such as change of diet, change of activities, etc. An incentive management module 115 may generate incentives based on health events, for example, such as incentives for regulation of vitals, adherence and exceeding prescribed goals, etc. A visualization system 116 may be provided for operation in conjunction with the collaborative healthcare system 100, or as a component (e.g., a visualization module) thereof, to display information related to a patient's healthcare plan and/or healthcare programs.

The modules and other components of the system 100 that perform various other functions in the system 100, may comprise machine readable instructions stored on a non-transitory computer readable medium. In addition, or alternatively, the modules and other components of the system 100 may comprise hardware or a combination of machine readable instructions and hardware.

Figure 2:
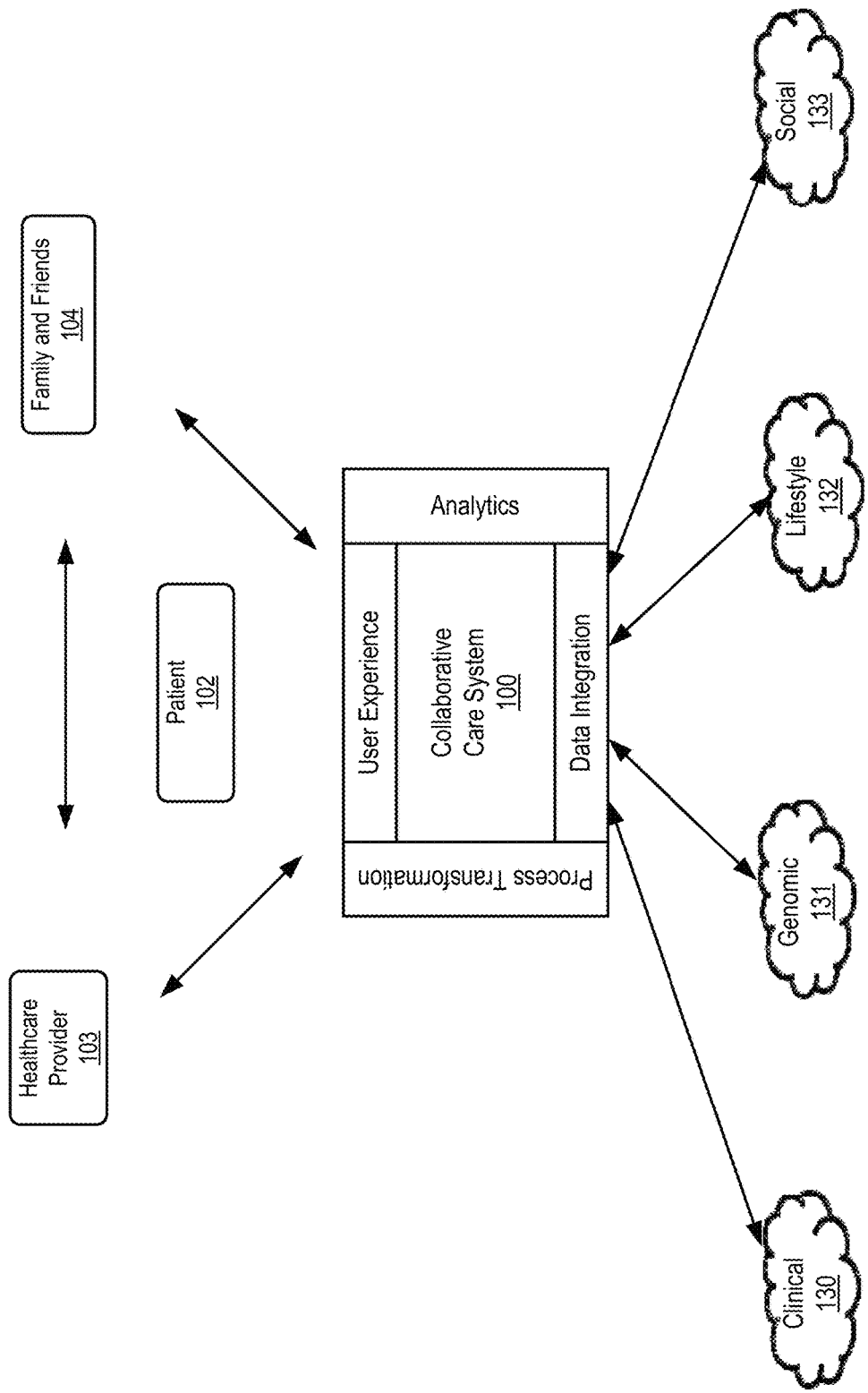
FIG. 2 illustrates a patient centered framework of the collaborative healthcare system, according to an example of the present disclosure.

Referring to FIGS. 1 and 2, FIG. 2 illustrates a patient centered framework of the collaborative healthcare system 100, according to an example of the present disclosure. The collaborative healthcare system 100 may generally receive and integrate data that may be categorized as clinical data 130, genomic data 131, lifestyle data 132, and social data 133 from the social networks 107. The clinical data 130 may include patient data (e.g., data from health information exchange, or electronic medical records) from sources such as hospitals, clinics, and generally, healthcare facilities. The genomic data 131 may include data related, for example, to recombinant DNA, DNA sequencing methods, and bioinformatics related to a patient. The lifestyle data 132 may include data related, for example, to a patient's activities from activity monitoring devices, such as, cell phones, heart rate monitors, smart pill boxes, etc. The social data 133 may include data related, for example, to third party sites, such as, PATIENTSLIKEME, FACEBOOK, TWITTER, etc. The social data 133 may be used, for example, to determine the patient's mood or infer their preferences based on activity on such third party sites. The patient centered framework of the collaborative healthcare system 100 may include a centralized data model that includes information related to a patient profile for each patient, and further includes information related to an overall healthcare plan for a patient. The patient centered framework of the collaborative healthcare system 100 may also include patient preferences (implied or stated), important occurrences in a patient's history, health literacy information, and incentives related, for example, to cost, clinical and social aspects.

Figure 3:
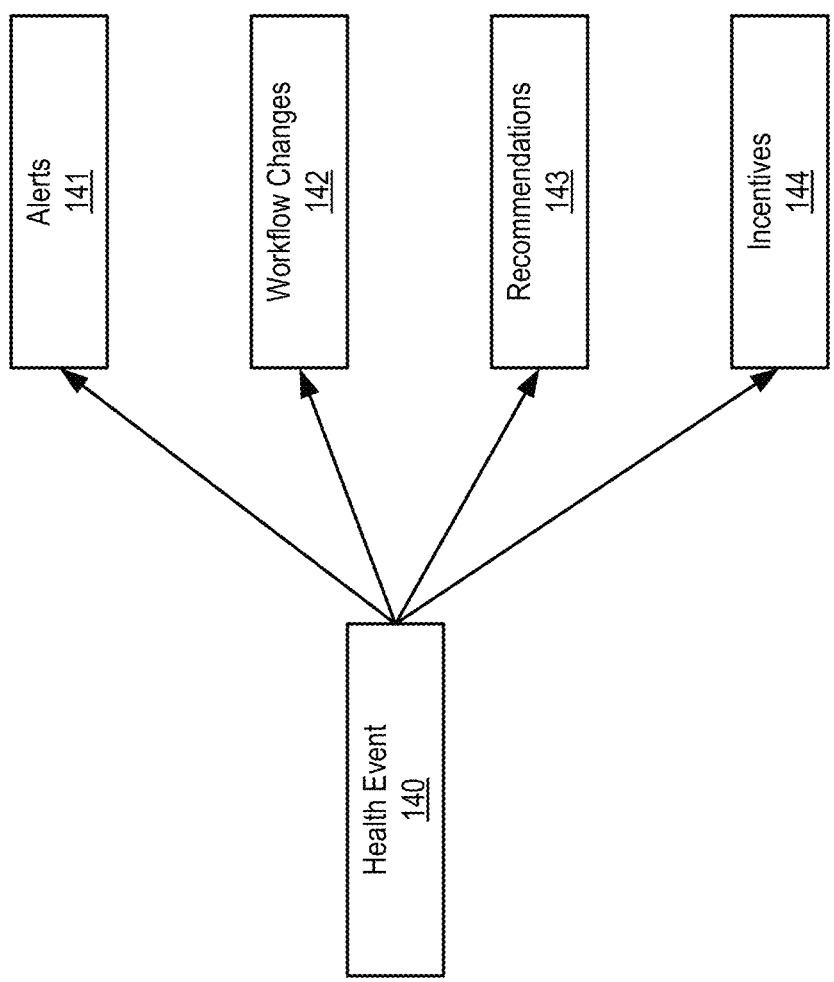
FIG. 3 illustrates a health event for the collaborative healthcare system, according to an example of the present disclosure.

Referring to FIGS. 1 and 3, FIG. 3 illustrates a health event 140 for the collaborative healthcare system 100, according to an example of the present disclosure. The health event 140 may be used by the event management module 111 to generate alerts 141, workflow changes 142, recommendations 143, and/or offer for incentives 144, as described in further detail below. The health event 140 may include any type of event that may impact the patient's health. Thus, based on the health event 140, the alerts 141 may be generated for use by the patient 102, members of the patient's healthcare provider 103, and/or the family and friends 104. The workflow automation module 112 may make adjustments to standard workflows, for example, by adding appointments (e.g., based on the workflows 142). The recommendation module 114 may provide recommendations to the healthcare provider 103 to address the health event 140. Further, the incentive management module 115 may provide the patient 102 with the incentives 144, for example, to facilitate health management.

Figure 4:
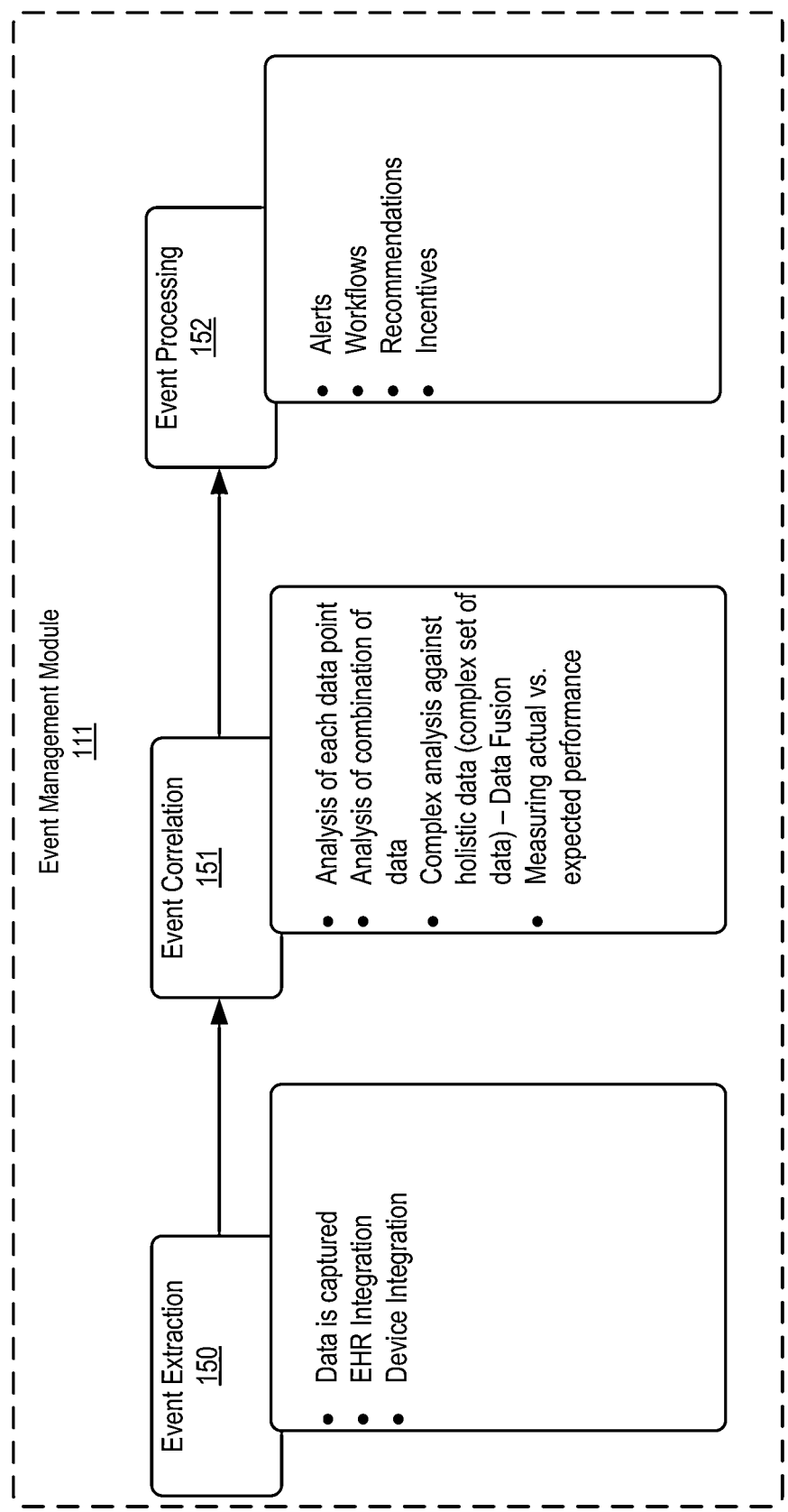
FIG. 4 illustrates further details of an event management module, according to an example of the present disclosure.

Referring to FIGS. 1, 3, and 4, FIG. 4 illustrates further details of the event management module 111, according to an example of the present disclosure. The event management module 111 may include event extraction 150 that includes data capture, electronic health record (EHR) integration, and device integration. The event management module 111 may further include event correlation 151 that includes analysis of each data point and/or combination of data. The event correlation 151 may further include complex analysis of holistic data, and measurement of actual versus expected performance. The event management module 111 may further include event processing 152 that includes the generation of alerts, workflows, recommendations, and incentives, as also shown in FIG. 3.

Figure 5:
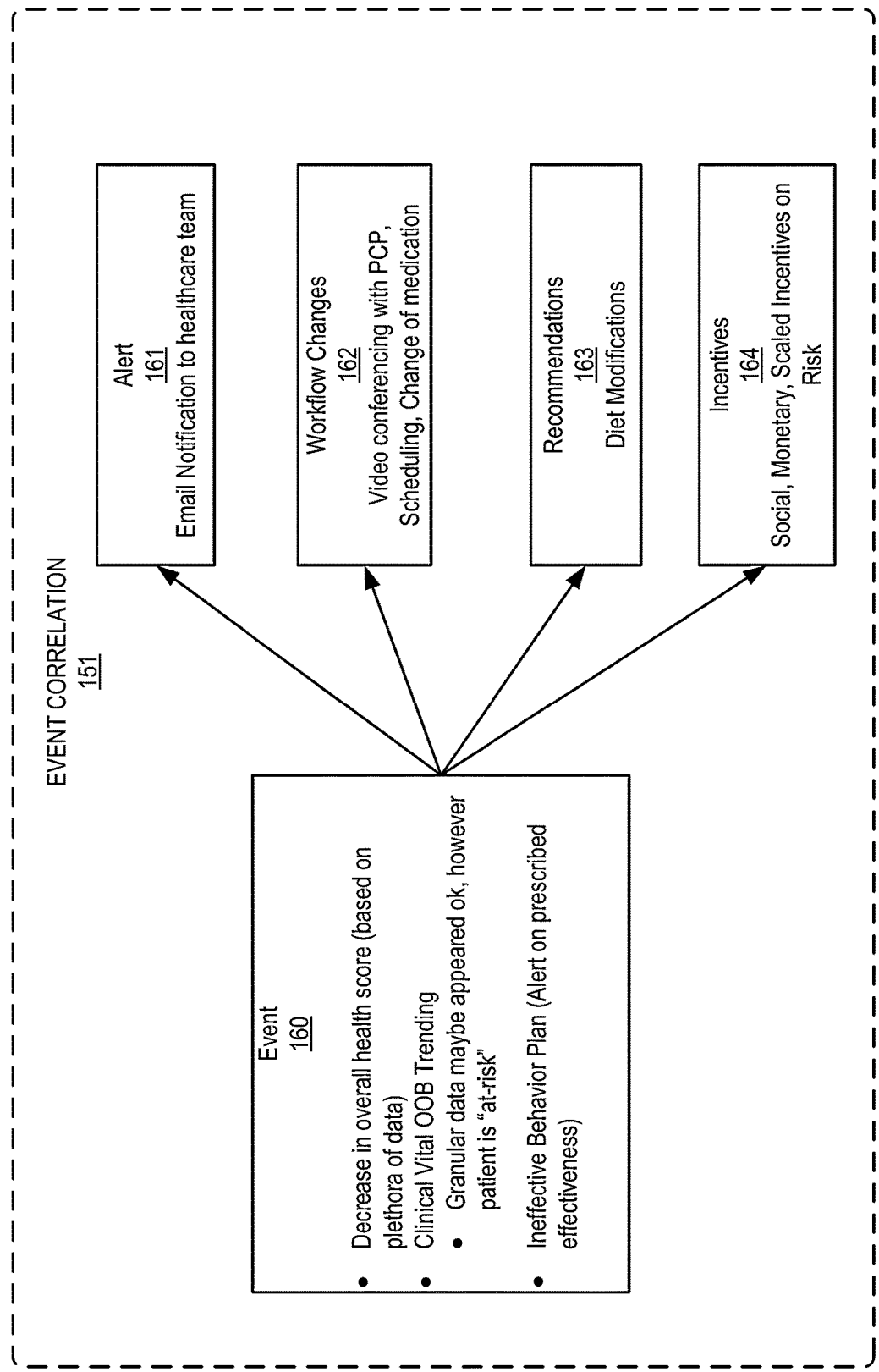
FIG. 5 illustrates event correlation for the collaborative healthcare system, according to an example of the present disclosure.

Referring to FIGS. 1, 4, and 5, FIG. 5 illustrates further details of the event correlation 151, according to an example of the present disclosure. As discussed for FIG. 3, the health event 140 may result in generation of alerts 141, workflow changes 142, recommendations 143, and/or offer for incentives 144. The health event 140 may be generally designated as an event 160 that results in generation of alerts 161, workflow changes 162, recommendations 163, and/or offer for incentives 164. The event 160 may be managed by the event management module 111 and may be based on a variety of health related events, such as, for example, a decrease in an overall health score, clinical vital out-of-band (OOB) trending (e.g., although granular data may appear to be acceptable, a patient may nevertheless be "at-risk"), and an ineffective behavior plan. The alert 161 may include, for example, an email notification being sent to a healthcare team. The workflow changes 162 may be managed by the workflow automation module 112 and may include, for example, scheduling a video conference with a preferred care provider (PCP), scheduling and in-person appointment, change of medication, etc. The recommendations 163 may be managed by the recommendation module 114 and may include, for example, diet modifications. The incentives 164 may be managed by the incentive management module 115 and may include, for example, social, monetary, and/or or scaled incentives based on risk.

Figure 6:
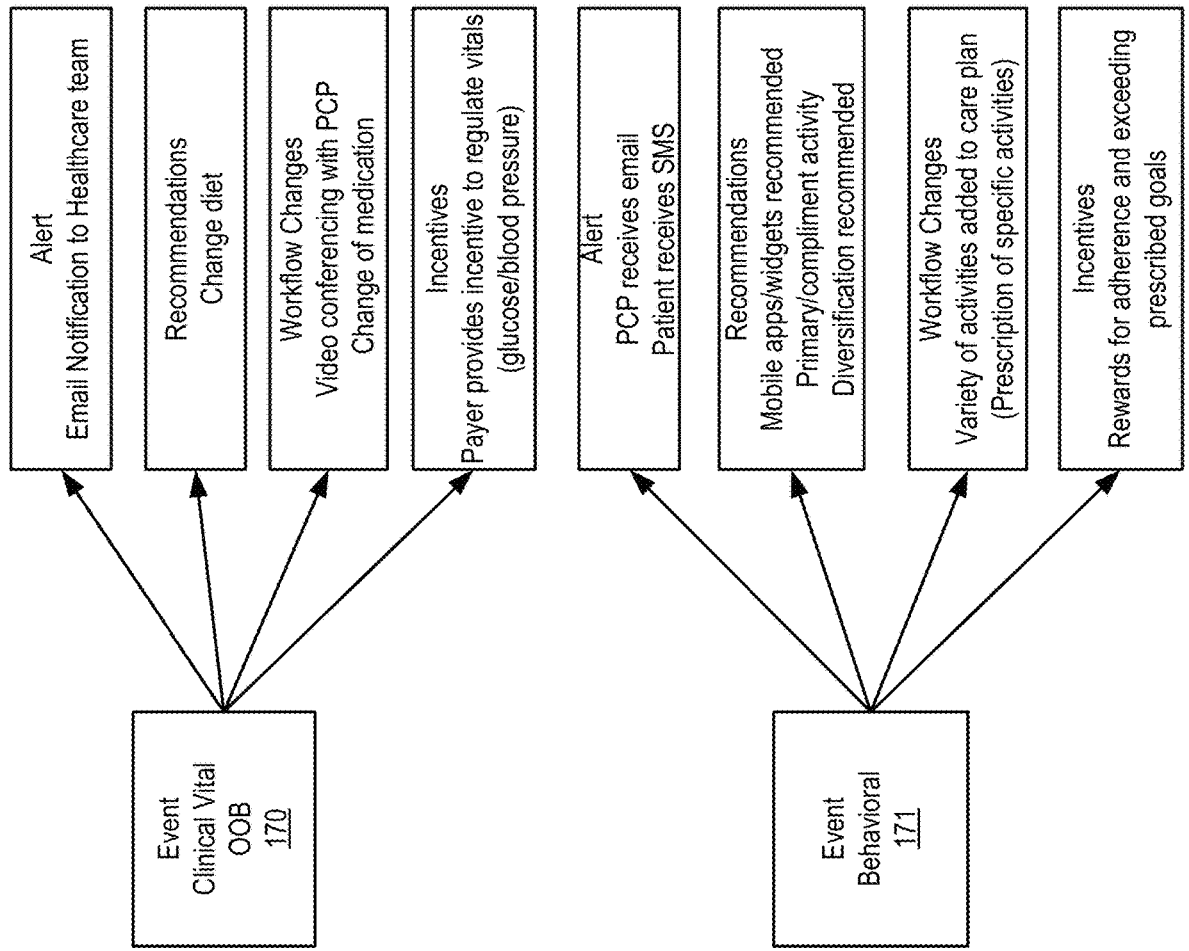
FIG. 6 illustrates health event processing for the collaborative healthcare system, according to an example of the present disclosure.

Referring to FIGS. 1, and 4-6, FIG. 6 illustrates health event processing for the collaborative healthcare system 100, according to an example of the present disclosure. As shown in FIG. 6, health events related to clinical vital OOB trending may be processed as shown at 170, and health events related to behavioral aspects (e.g., patient consumes too may or too few calories) may be processed as shown at 171. The health events related to clinical vital OOB trending and the health events related to behavioral aspects may be managed by the event management module 111. For example, for health events related to clinical vital OOB trending at 170, an alert may include, for example, an email notification being sent to a healthcare team, recommendations may include, for example, diet modifications, workflow may include, for example, video conferencing with a PCP, change of medication, etc., and incentives may include, for example, incentives provided by a payer to regulate vitals. Further, for health events related to behavior at 171, an alert may include, for example, an email notification being sent to a PCP and/or a short message service (SMS) being sent to a patient, recommendations may include, for example, mobile applications and widgets to assist the patient in dealing with the specific health event, primary and compliment activities to deal with the specific health event, and diversification, workflow may include, for example, a variety of activities added to a healthcare plan (e.g., prescription of specific activities), and incentives may include, for example, rewards for adherence to and/or exceeding prescribed goals.

Figure 7:
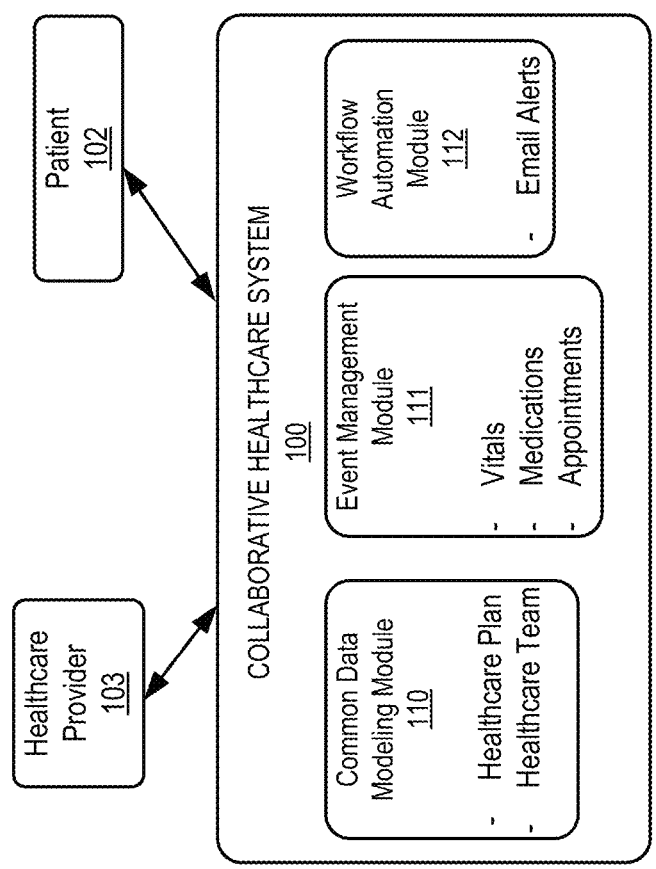
FIG. 7 illustrates continuity of healthcare for the collaborative healthcare system, according to an example of the present disclosure.

Referring to FIGS. 1 and 7, FIG. 7 illustrates continuity of healthcare for the collaborative healthcare system 100, according to an example of the present disclosure. Continuity of healthcare (e.g., healthcare provided after initial input and analysis of patient data) for the collaborative healthcare system 100 may include orchestration of patient and healthcare provider interactions, for example, for the patient 102 and the healthcare provider 103 of FIG. 1. For example, continuity of healthcare may include use of the common data modeling module 110 to model common data related, for example, to a healthcare plan and a healthcare team. Continuity of healthcare may further include use of the event management module 111 to process events related, for example, to patient vitals, medications, appointments, etc. Further, continuity of healthcare may include use of the workflow automation module 112 to provide, for example, automatic scheduling of appointments with a specialist based on health events.

Figure 8:
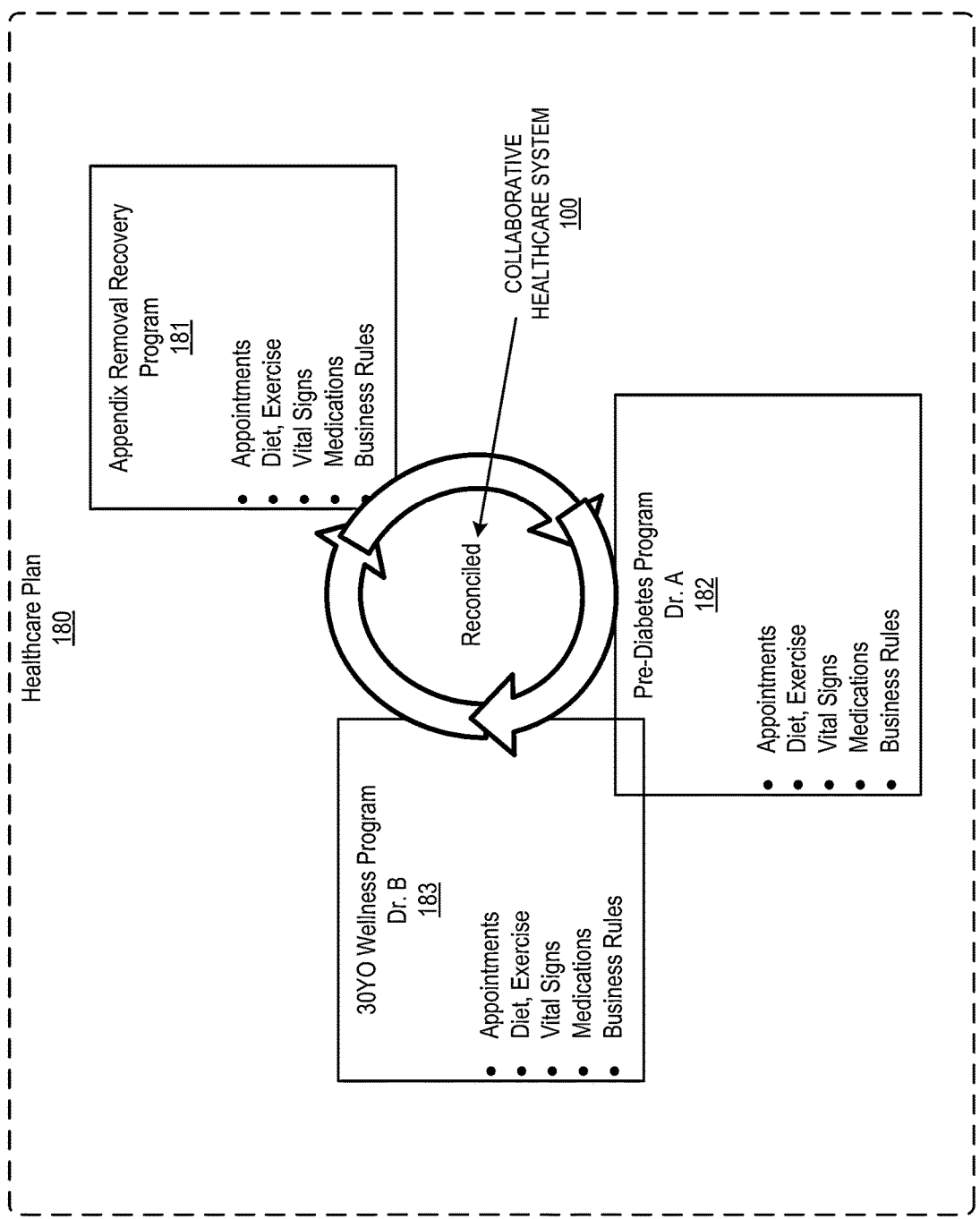
FIG. 8 illustrates a healthcare plan including a plurality of healthcare programs for the collaborative healthcare system, according to an example of the present disclosure.

Referring to FIGS. 1 and 8, FIG. 8 illustrates a healthcare plan 180 including a plurality of healthcare programs for the collaborative healthcare system 100, according to an example of the present disclosure. For example, the healthcare plan 180 may include an appendix removal recovery program 181, a pre-diabetes program 182 with a Dr. A, and a thirty year old wellness program 183 with a Dr. B. The healthcare programs 181-183 that form the healthcare plan 180 may be reconciled by the collaborative healthcare system 100. Each of the healthcare programs 181-183 may include information related, for example, to appointments, diet and exercise, vital signs, medications, and business rules. Thus, different healthcare providers (e.g., doctors) may be provided with the universal view of the patient's overall healthcare, and may be further provided with healthcare provider-specific views (e.g., healthcare program views) of the patient's healthcare based on automatic reconciliation of the healthcare programs 181-183 that form the patient's healthcare plan.

Figure 9:
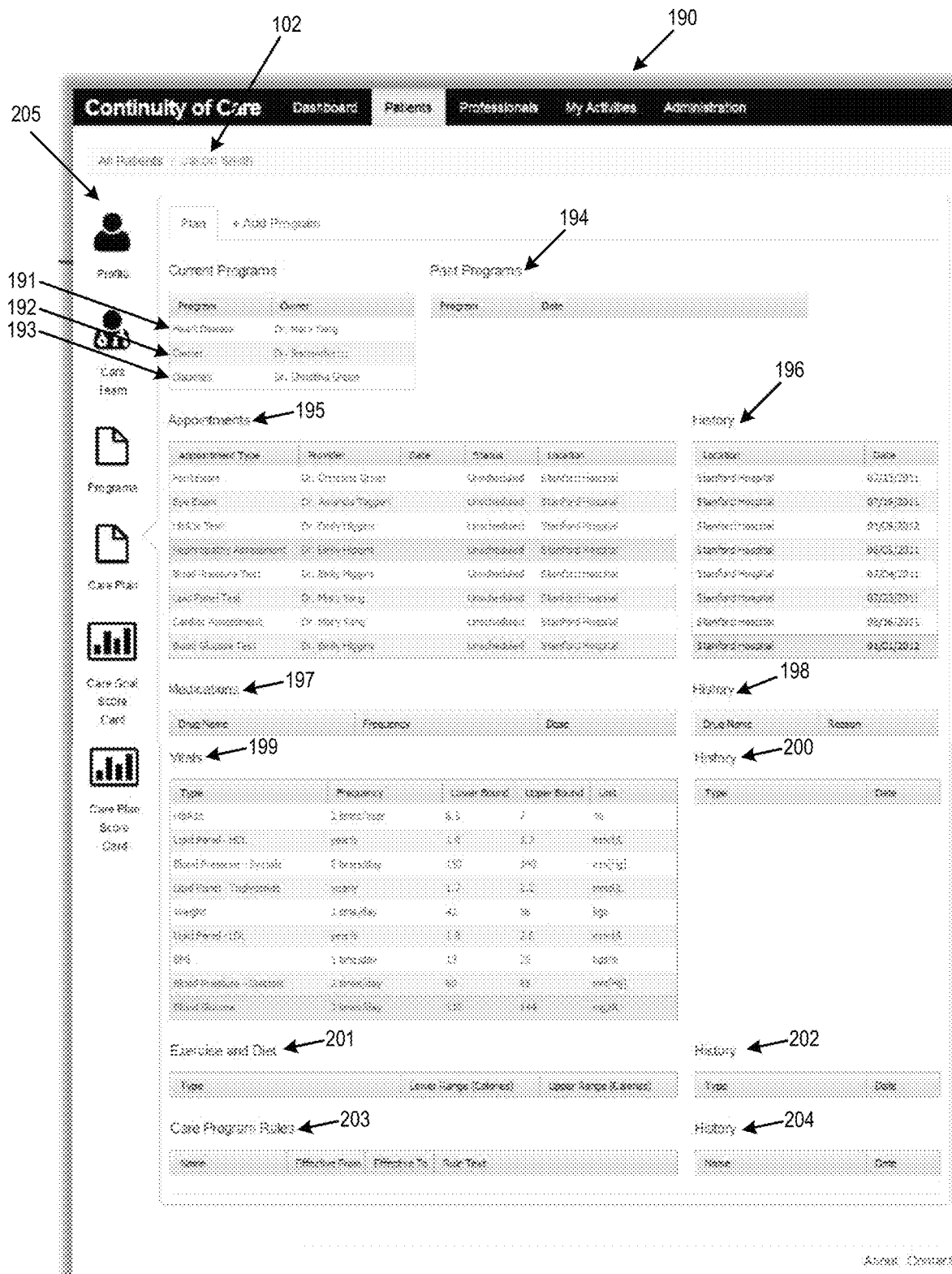
FIG. 9 illustrates a user interface (UI) display for a healthcare plan for the collaborative healthcare system, according to an example of the present disclosure.

Referring to FIGS. 1 and 9, FIG. 9 illustrates a user interface (UI) display for a healthcare plan 190 for the collaborative healthcare system 100, according to an example of the present disclosure. The healthcare plan 190 may include healthcare programs 191-193. For example, the healthcare programs 191-193 may be respectively related to heart disease, cancer, and diabetes for the patient 102. The healthcare plan 190 may include past programs at 194, upcoming appointments at 195, appointment history at 196, medications at 197, medication history at 198, vitals at 199, vital history at 200, exercise and diet at 201, exercise and diet history at 202, care program rules at 203, and care program rules history at 204. The healthcare plan 190 may include a menu of selectable items at 205 that may include a patient profile, healthcare team information, healthcare programs, healthcare plan, healthcare goal score card, and healthcare plan score card. Thus the patient 102 may be provided with a universal view of the patient's overall healthcare plan based on automatic reconciliation of a plurality of healthcare programs (e.g., healthcare programs 191-193) that form the patient's healthcare plan 190.

Referring to FIGS. 1 and 10, FIG. 10 illustrates a UI display for a pre-diabetes program 210 for the collaborative healthcare system 100, according to an example of the present disclosure. The pre-diabetes program 210 may include the categories of appointments, diet and exercise, vital signs, medications, and abbreviated business rules in column 211, and information related to the categories of column 211 in column 212. Based on the information in column 212, a variety of alerts and recommendations may be triggered. For example, referring to FIG. 11, FIG. 11 illustrates triggers and actions for the pre-diabetes program of FIG. 10, according to an example of the present disclosure. Referring to FIG. 11, based on the examples of triggers listed in column 220, actions at 221 may be recommended and/or performed. For example, as shown at 222, if a metformin Rx is not picked up, based on analysis performed by the rules module 108, actions such as recommendation of a less expensive Rx may be performed, for example, by the event management and recommendation modules 111, 114. After one week of the metformin Rx not being picked up, an email reminder may be sent to the patient 102. Further, as shown at 223, the rules module 108 may include rules that provide alerts to providers if a patient's vitals are trending out of normal range. Thus, based on the various triggers listed in column 220, actions at 221 may be recommended and/or performed for the patient 102.

Figure 12:
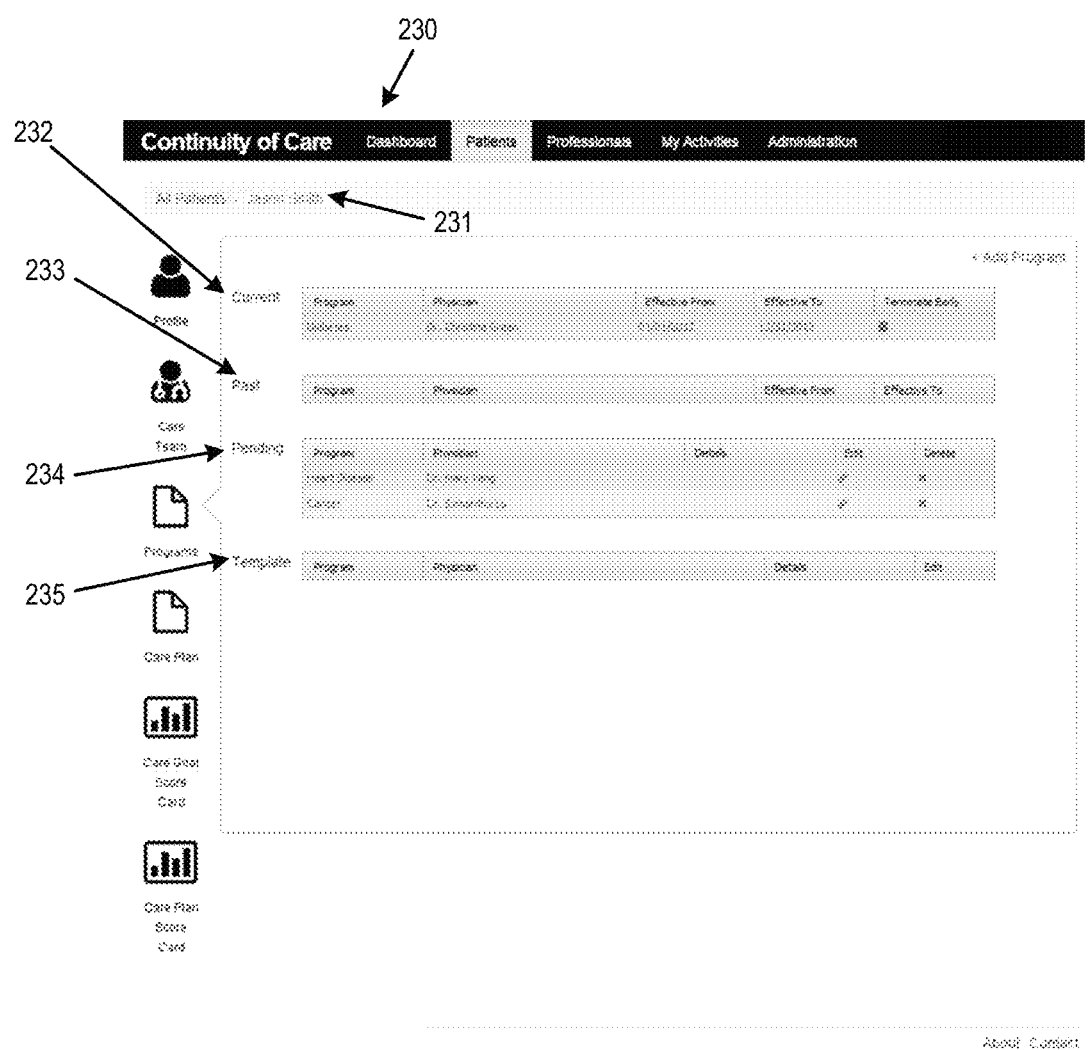
FIG. 12 illustrates a UI display for healthcare programs for continuity of healthcare for the collaborative healthcare system, according to an example of the present disclosure.
Figure 13:
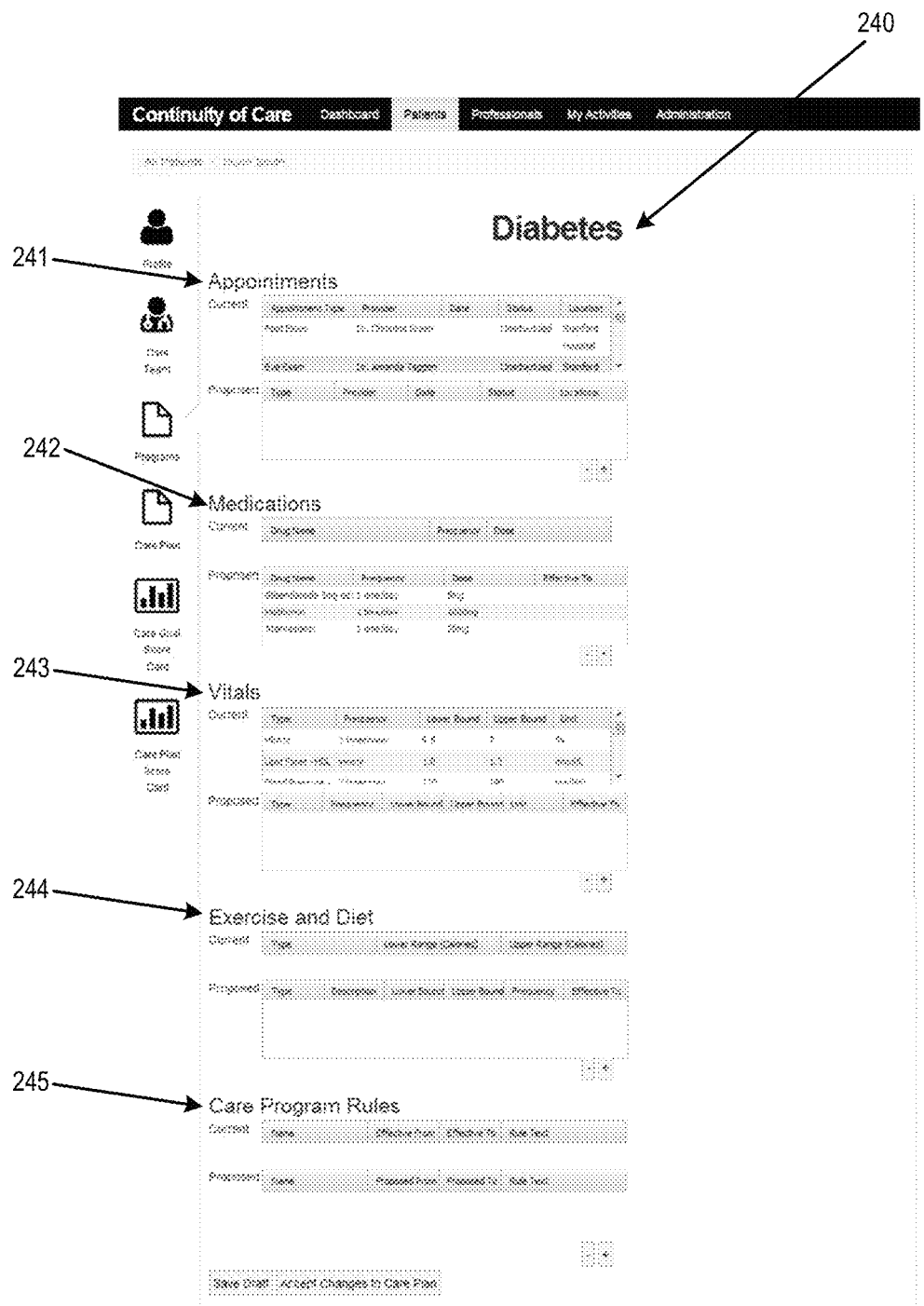
FIG. 13 illustrates a UI display for details of a diabetes care program for the collaborative healthcare system, according to an example of the present disclosure.

Referring to FIGS. 1 and 12, FIG. 12 illustrates a UI display 230 for healthcare programs for continuity of healthcare for the collaborative healthcare system 100, according to an example of the present disclosure. Referring to FIGS. 1, 7, and 12, the UI display 230 may include a patient's name at 231, current, past (i.e., completed), and pending (i.e., planned) healthcare programs respectively at 232-234, and a template of healthcare programs at 235. FIG. 13 illustrates a UI display for details of a diabetes care program 240 for the collaborative healthcare system 100, according to an example of the present disclosure. Referring to FIGS. 12 and 13, for the diabetes care program 240 listed under the current healthcare programs at 232, details related to appointments, medications, vitals, exercise and diet, and business rules (i.e., healthcare program rules) may be provided, respectively, at 241-245. Thus, different healthcare providers (e.g., doctors) may be provided with the universal view of the patient's overall healthcare, and may be further provided with healthcare provider-specific views (e.g., healthcare program views such as the diabetes care program 240) of the patient's healthcare based on automatic reconciliation of the plurality of healthcare programs that form the patient's healthcare plan.

Referring to FIG. 13, with respect to the business rules (i.e., healthcare program rules) at 245, treatment actions for the patient 102 may be seen as the result of a series of business rules, based on the specific condition being treated. For example, for a cardiovascular patient, the rules module 108 may analyze business rules as follows:

```
if BLOOD PRESSURE (measured 3x/day) is OUT OF BOUNDS > 3
TIMES IN A ROW
    then ALERT the CARDIOLOGIST ← (alert*)
    and SCHEDULE VIDEOCONF APPOINTMENT with
CARDIOLOGIST ← (schedule appointment**)
    and TEST BLOOD PRESSURE MORE FREQUENTLY (4x/day) ←
(modify program***)
    and MODIFY THE RULE ON BLOOD PRESSURE TO ONLY
ALERT IF OOB > 4 TIMES IN A ROW
```

By codifying treatment into a series of rules which operate on live data, the collaborative healthcare system 100 may generate alerts and/or alarms on current or trending conditions, create ad-hoc appointments and referrals, and generate suggestions for the healthcare provider 103 about other healthcare plan modifications that the healthcare provider 103 may make (e.g., modifications related to vitals, medications, diet, exercise, etc.). The rules module 108 may also provide for authoring of rules such that the healthcare provider 103 may create meaningful and useful rules to shape the path of the patient 102 to wellness (or condition maintenance). Similar to other program components (e.g., vitals, appointments, medications, and lifestyle), the healthcare plan reconciliation module 101 may process these rules to ensure that there are no conflicts between rules, and the rules are designed for specific components of the healthcare plan.

Figure 14:
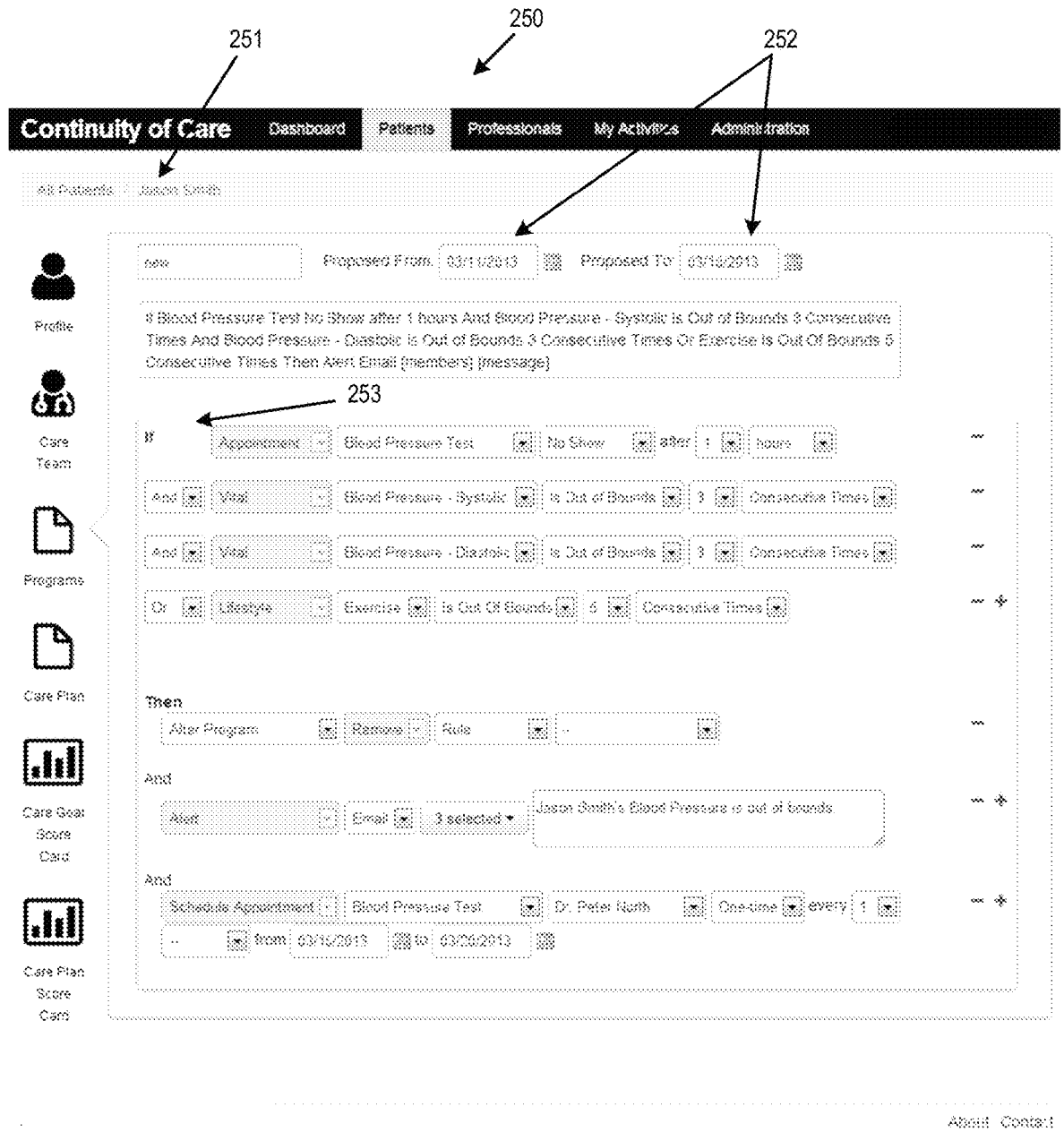
FIG. 14 illustrates a business rules authoring UI for the collaborative healthcare system, according to an example of the present disclosure.

Referring to FIGS. 1 and 14, FIG. 14 illustrates a business rules authoring UI 250 for the collaborative healthcare system 100, according to an example of the present disclosure. The business rules authoring UI 250 may generally include a patient designation at 251, a from/to time period designation at 252, and pre-determined components 253 for generating business rules. Thus, once a from/to time period is designated at 252, the healthcare program associated with the business rules may be reconciled with other healthcare programs for the patient 102 by the healthcare plan reconciliation module 101 for the from/to time period designated at 252.

Figure 15:
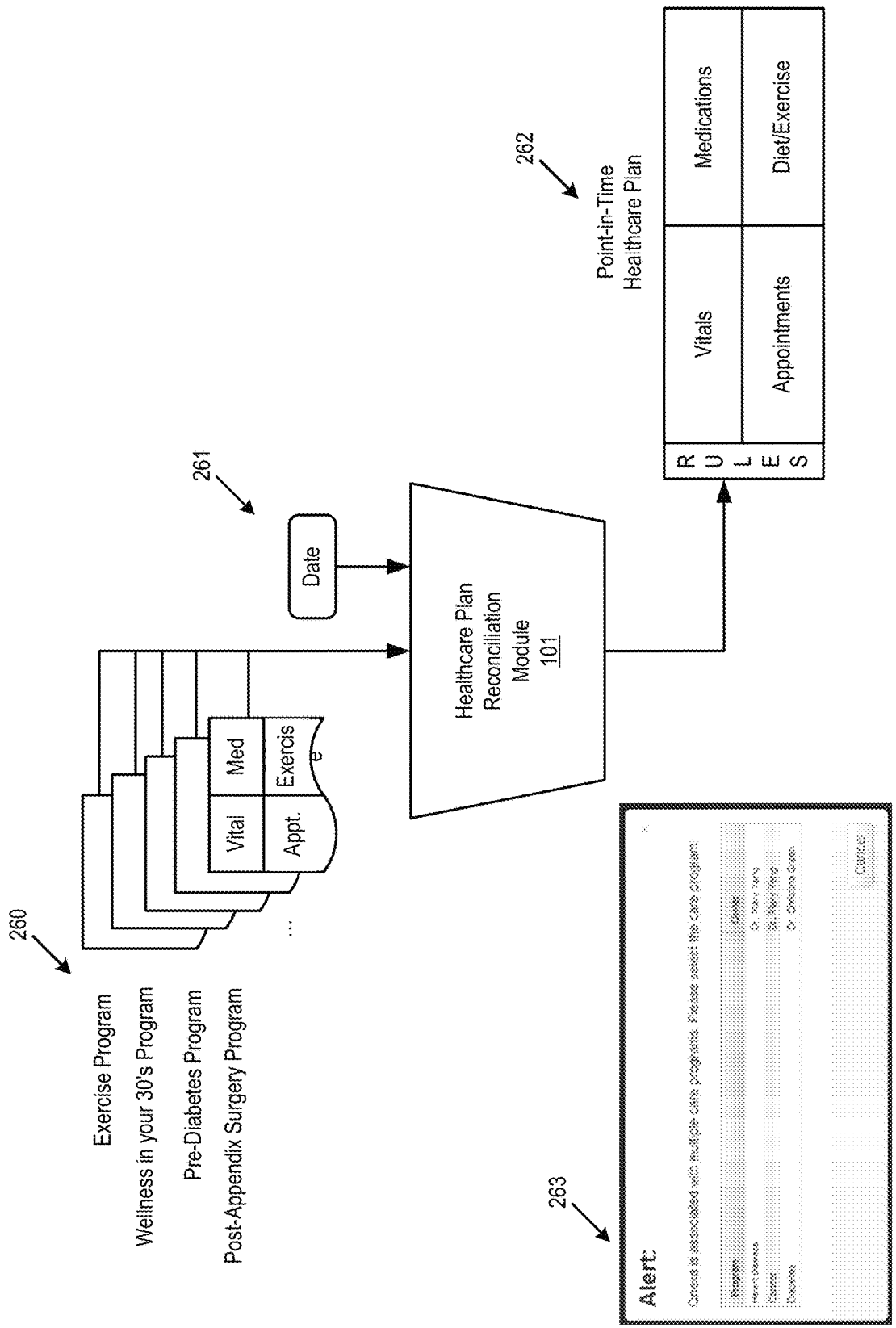
FIG. 15 illustrates application of a healthcare plan reconciliation module of the collaborative healthcare system, according to an example of the present disclosure.

Referring to FIGS. 1 and 15, FIG. 15 illustrates application of the healthcare plan reconciliation module 101 for the collaborative healthcare system 100, according to an example of the present disclosure. The healthcare plan reconciliation module 101 may receive a plurality of healthcare programs 260 that designate a healthcare plan for the patient 102. For example, the healthcare programs 260 may include exercise, wellness, pre-diabetes, and post-appendix surgery programs for the patient 102. Each of the programs may be received by the healthcare plan reconciliation module 101 along with a period 261 (e.g., 1 year, 2 years, etc.) for reconciliation. The healthcare plan reconciliation module 101 may operate in conjunction with the rules module 108 to generate a point-in-time healthcare plan 262 for the patient 102. Thus the patient 102 may be provided with a universal view of the patient's overall healthcare plan (e.g., the point-in-time healthcare plan 262) based on automatic reconciliation of a plurality of healthcare programs (e.g., the healthcare programs 260) that form the patient's healthcare plan. When an item is common to multiple healthcare programs, the healthcare plan reconciliation module 101 may generate alerts at 263.

Figure 16:
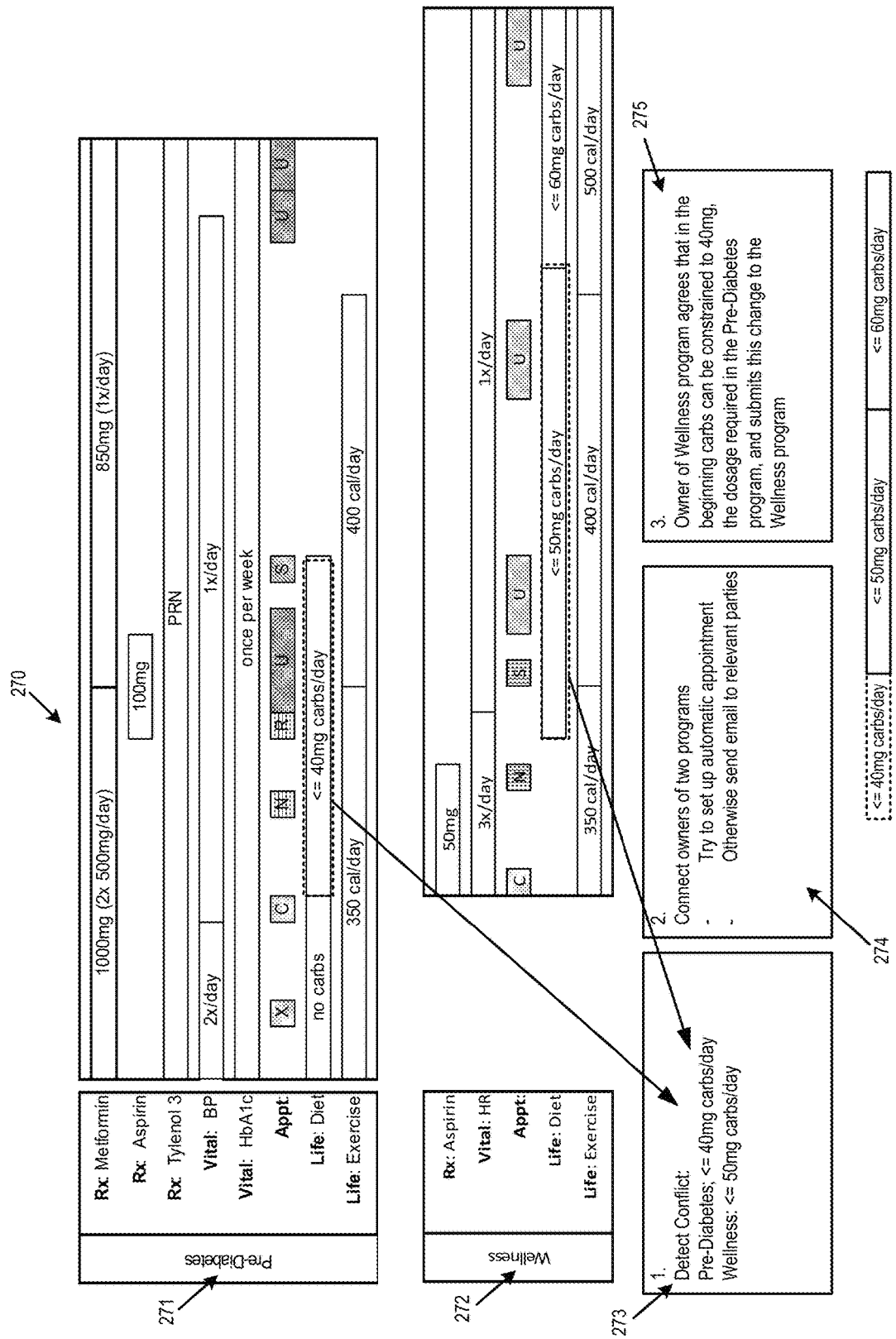
FIG. 16 illustrates a UI display for details of conflict resolution for the collaborative healthcare system, according to an example of the present disclosure.

Referring to FIGS. 1 and 16, FIG. 16 illustrates a UI display 270 for details of conflict resolution by the healthcare plan reconciliation module 101, according to an example of the present disclosure. The healthcare plan reconciliation module 101 may resolve conflicts between healthcare programs. For example, operation of the healthcare plan reconciliation module 101 is illustrated for resolving conflicts between a pre-diabetes program 271 and a wellness program 272. For example, at 273, a conflict in the pre-diabetes program 271 for less than or equal to 40 mg carbs/day and the wellness program 272 for less than or equal to 50 mg carbs/day may be detected. At 274, the reconciliation module 101 may connect owners (i.e., the healthcare providers 103) of the pre-diabetes program 271 and the wellness program 272. At 275, if the owner of the wellness program 272 agrees to the carbs being constrained to 40 mg/day, these changes may be entered into the wellness program 272. Thus the patient 102 may be provided with a universal view of the patient's overall healthcare plan based on automatic reconciliation of a plurality of healthcare programs (e.g., the pre-diabetes program 271 and the wellness program 272) that form the patient's healthcare plan. Similarly, during reconciliation of healthcare programs into the patient's healthcare plan, a conflict may be found with other components of a patient's healthcare programs, such as medications prescribed to the patient by different physicians that when taken together produce adverse outcomes. The healthcare plan reconciliation module 101 may detect such conflicts and similarly engage physicians in a collaborative manner in a process which guides resolution of the conflict and determination of the best medication prescription.

Figure 17:
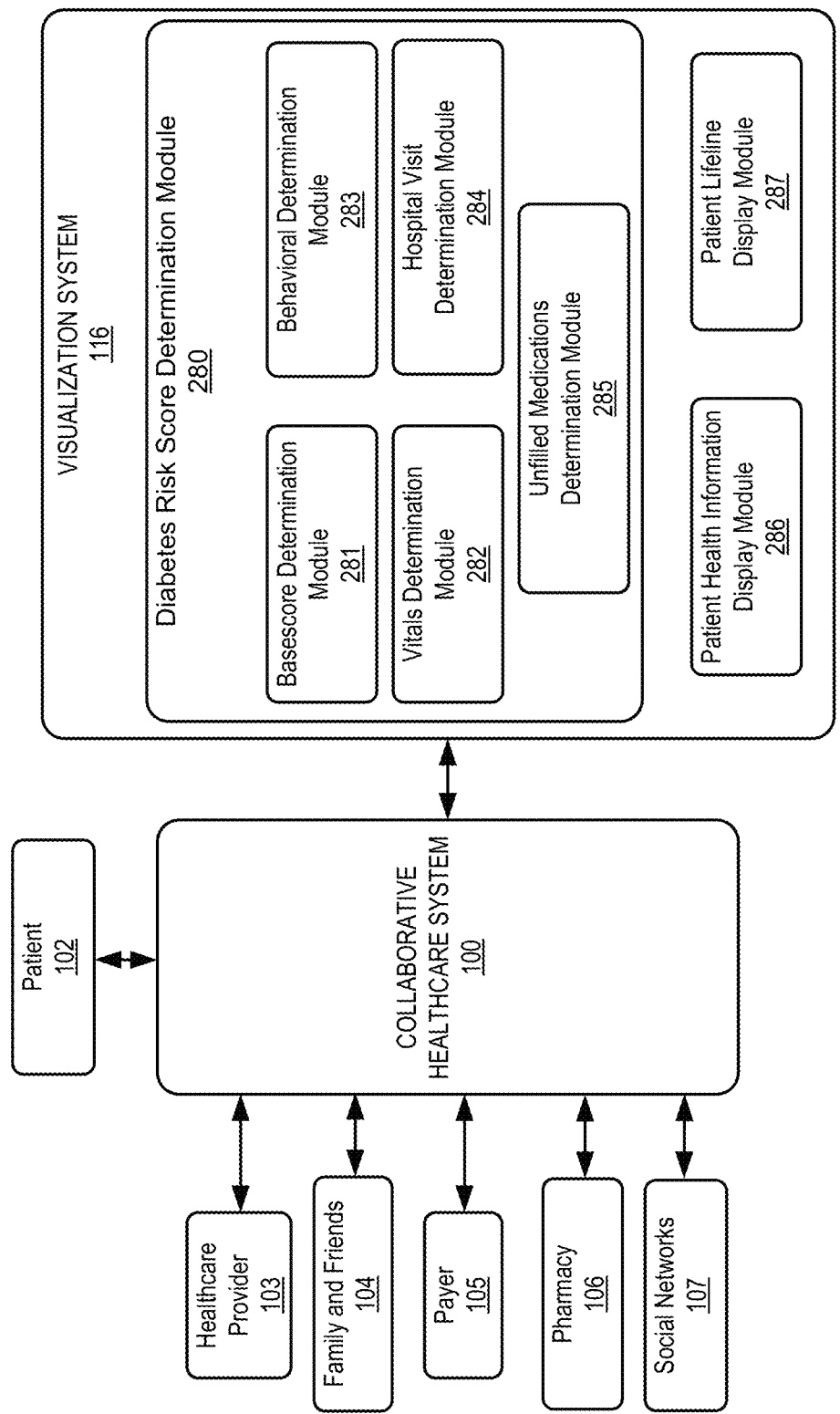
FIG. 17 illustrates further details of a visualization system associated with the collaborative healthcare system, according to an example of the present disclosure.

Referring to FIGS. 1 and 17, FIG. 17 illustrates the visualization system 116, according to an example of the present disclosure. The visualization system 116 may generally include a diabetes risk score determination module 280. The diabetes risk score determination module 280 may include a basescore determination module 281 to determine a base diabetes score component of the diabetes risk score. A vitals determination module 282 may determine a patient vitals component, for example, related to cholesterol, blood glucose, and blood pressure, for determining the diabetes risk score. A behavioral determination module 283 may determine a patient behavioral component, for example, related to missed medications, cancelled appointments, missed appointments, and calories (e.g., calorie fluctuation), for determining the diabetes risk score. A hospital visit determination module 284 may determine a hospital visit component, for example, related to emergency hospital visits, and inpatient hospital visits, for determining the diabetes risk score. An unfilled medications determination module 285 may determine an unfilled medications component, for example, related to prescriptions that have not been filled to date, for determining the diabetes risk score. A patient health information display module 286 may display (using a UI) a variety of factors related to a patient's healthcare plan, such as drug and supplement usage, healthcare encounters, vitals, mood, and check-ins. A patient lifeline display module 287 may display (using a UI) a lifeline of an overall score representative of the patient's health based on an analysis of individual healthcare related signals from the patient health information display module 286, and other factors related to the patient's health.

Figure 18:
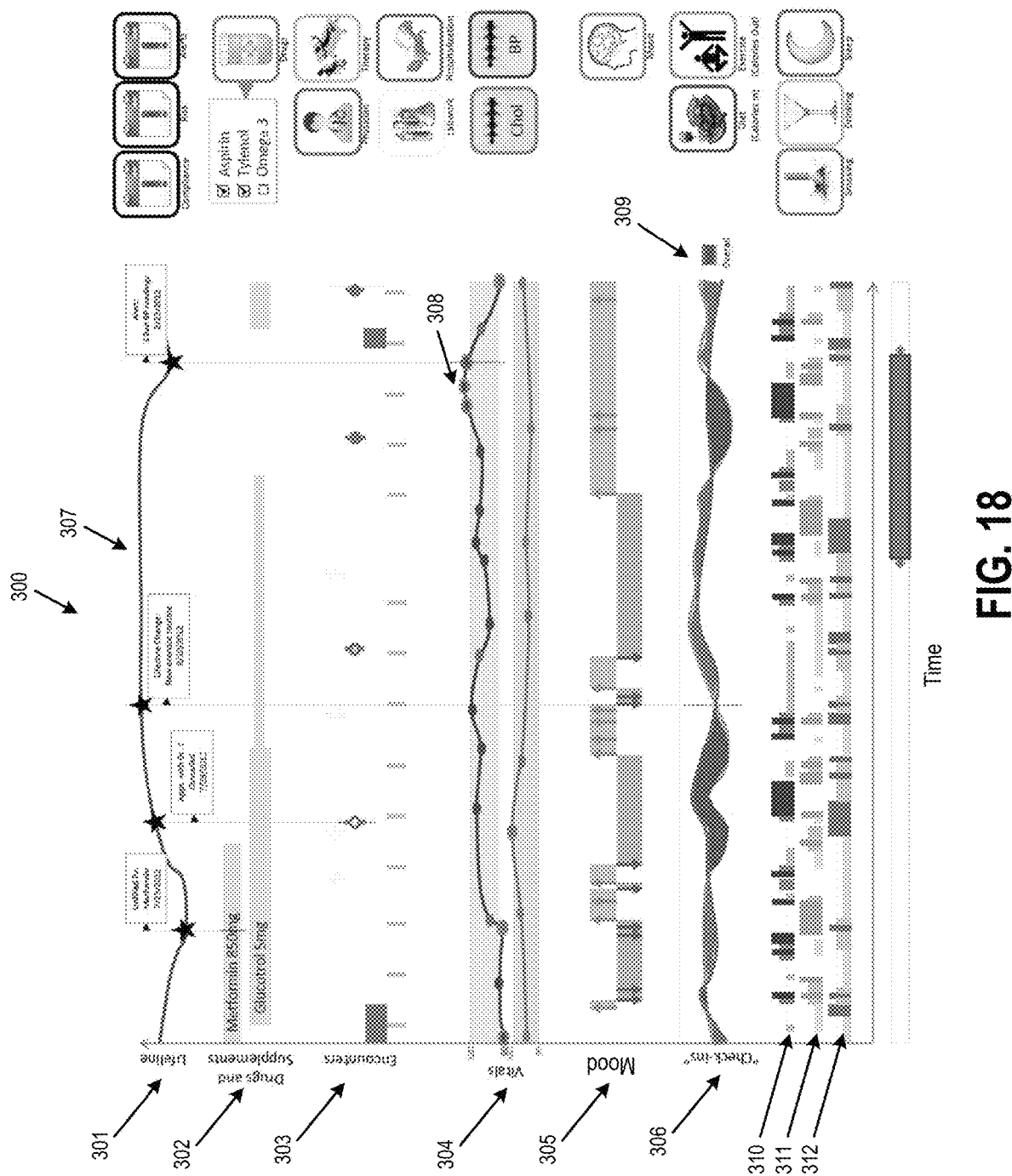
FIG. 18 illustrates a visualization system display, according to an example of the present disclosure.

Referring to FIGS. 1 and 18, FIG. 18 illustrates a visualization system display 300 provided by the patient health information display module 286, according to an example of the present disclosure. The visualization system display 300 may be provided on a common horizontal axis that is, for example, a time axis. The different aspects that may influence the patient's health may be displayed using colors and/or symbols along the vertical axis. For example, the vertical axis may include information related to drug and supplement usage at 302, healthcare encounters at 303, vitals at 304, mood at 305, and check-ins at 306. In order to facilitate comprehension of the visualization system display 300, graphics related to the information may be provided at 307. For example, the drug and supplement usage at 302 may show the type of medication and when the medication use tapers. The visualization system display 300 may also show appointments, and whether the appointments are scheduled, completed, etc. Other healthcare encounters at 303 may show encounters with physicians, therapists, lab work, hospitalization, etc. The vitals at 304 may be related, for example, to cholesterol, blood pressure, etc. Any OOB vitals may be displayed, for example, at 308. The mood at 305 may be related, for example, to the patient's mood (e.g., high, low, etc.). The check-ins at 306 may be related, for example, to diet and exercise, with calorie intake being displayed using a color red, and calorie output (e.g., by exercise) being displayed using a color blue. An overall calorie value may be displayed at 309. Other aspects related to patient behavior, such as, smoking, drinking, sleeping, etc., may be displayed at 310-312, respectively. The lifeline depicted at 301 may display an overall score representative of the patient's health based on an analysis of the individual signals (e.g., signals 302-306 and 310-312), and other factors related to the patient's health. Thus, the visualization system display 300 may provide the patient 102 with a universal view of the patient's overall healthcare in a graphical format based on automatic reconciliation of a plurality of healthcare programs that form the patient's healthcare plan. Further, the visualization system display 300 may provide different healthcare providers (e.g., doctors) with the universal view of the patient's overall healthcare, and healthcare provider-specific views (e.g., healthcare program views) of the patient's healthcare in a graphical format based on automatic reconciliation of the plurality of healthcare programs that form the patient's healthcare plan. The visualization system display 300 may thus be used to analyze impact of various factors to a patient's overall health.

Figure 19:
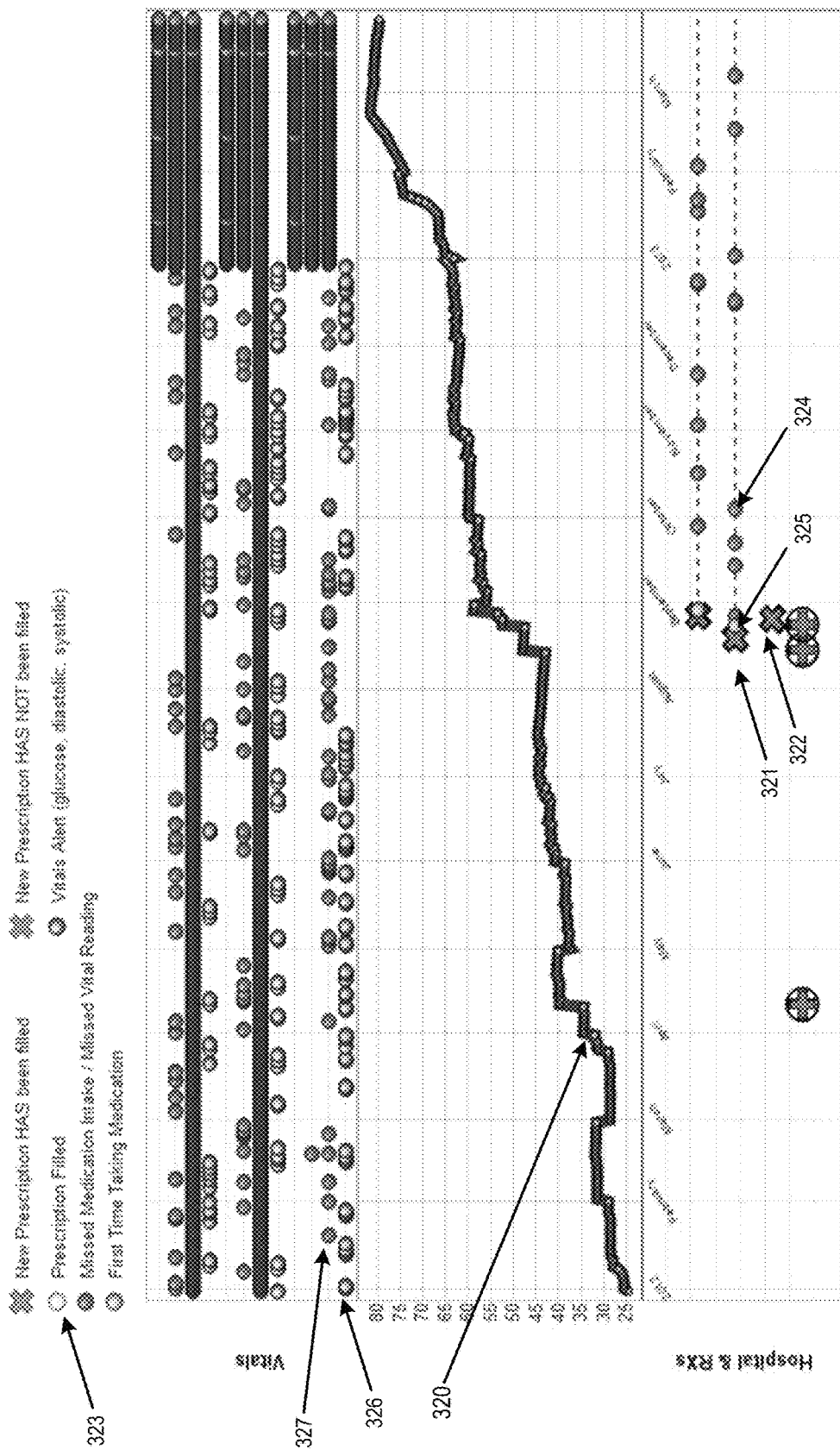
FIG. 19 illustrates a lifeline display for diabetes risk, according to an example of the present disclosure.
Figure 20:
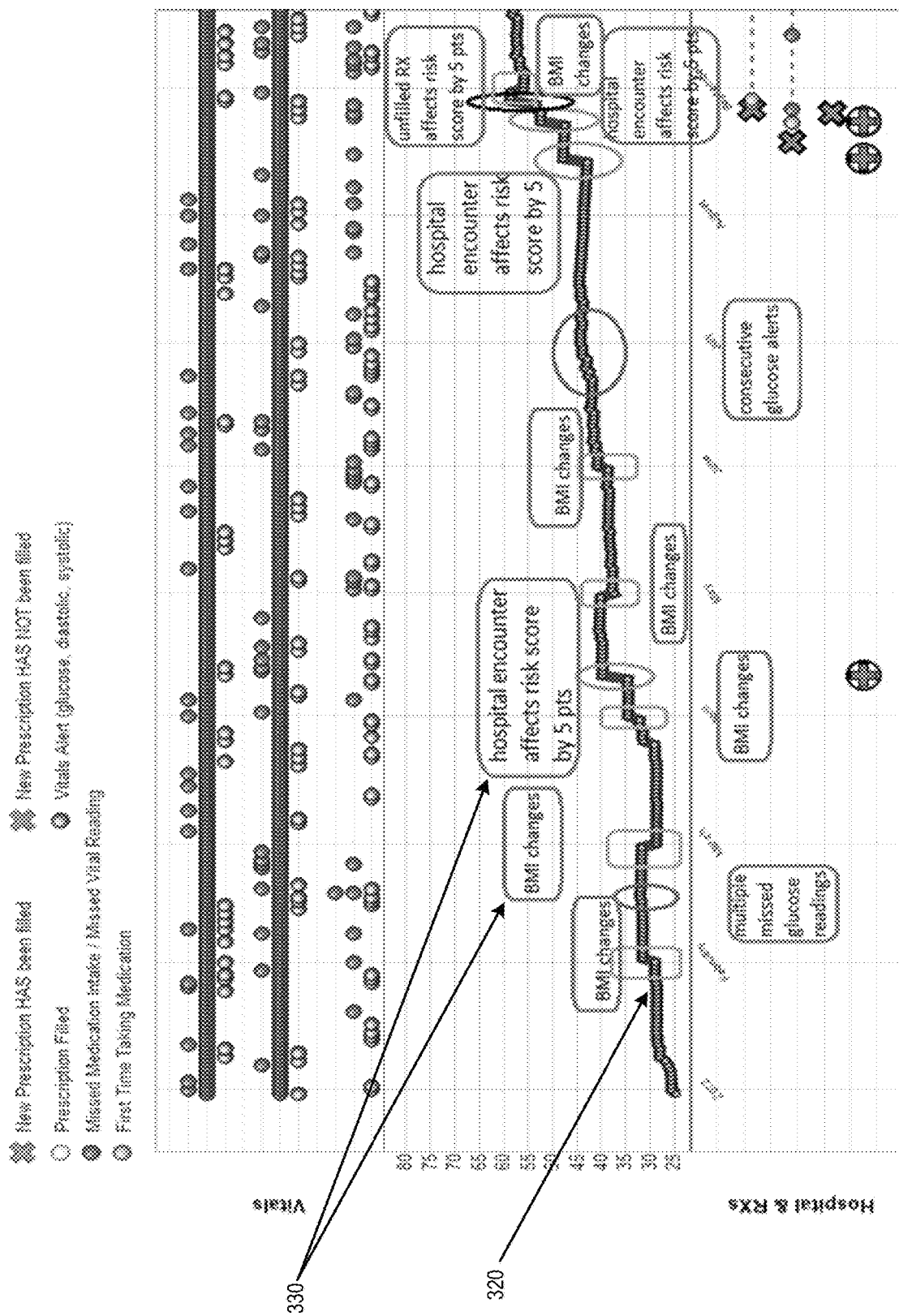
FIG. 20 illustrates further details of the lifeline display of FIG. 19, according to an example of the present disclosure.

Referring to FIGS. 1, 17, 19, and 20, FIG. 19 illustrates a lifeline display 320 provided by the patient lifeline display module 287 for diabetes risk, and FIG. 20 illustrates further details of the lifeline display 320 of FIG. 19, according to an example of the present disclosure. For example, FIG. 19 illustrates the lifeline display 320, new prescriptions that have been filled at 321, new prescriptions that have not been filled at 322, whether a prescription has been filled at 323, missed medication intake at 324 and missed vital readings at 327, first time taking a medication at 325, and vitals alert at 326. Referring to FIG. 20, further details of the lifeline display 320 of FIG. 19 may include notations, for example, at 330 that indicate various changes in the lifeline display 320.

Referring to FIGS. 1 and 17, the diabetes risk score determination module 280 may generally use the basescore determination module 281, the vitals determination module 282, the behavioral determination module 283, the hospital visit determination module 284, and the unfilled medications determination module 285 to determine a lifeline display, such as the lifeline display 320, for diabetes risk. For example, the diabetes risk score determination module 280 may determine a lifeline display for diabetes risk based on the following equation:

$$\text{Diabetes Risk Score} = \text{baseScore} + (90 - \text{baseScore})[\alpha * \text{vitals} + \beta * \text{behavioral}] + 5 * \text{hospital} + 5 * \text{unfilled\_medications} + \varepsilon \quad \text{Equation (1)}$$

For Equation (1), baseScore may represent the base diabetes score for the patient 102, and baseScore ≤90. For the diabetes risk score, $\alpha$ and $\beta$ may represent weights placed on the variables vitals and behavioral, both of which affect a patient's overall risk score. Further, $\beta = 1 - \alpha$, and $0 \leq \alpha \leq 1$, where $\alpha$ and $\beta$ may range from 0%-100% such that $\alpha + \beta = 100\%$. According to an example, $\alpha$ and $\beta$ may be tuned so that setting $\alpha = 0.7$ and $\beta = 0.3$ provides reasonable results for the diabetes risk score. Vitals may include cholesterol, blood glucose, and blood pressure. Behavioral aspects may include missed medications, cancelled appointments, missed appointments, and calories. Hospital visits may include emergency hospital visits, and inpatient hospital visits. Unfilled medications may include prescriptions that have never been filled to date. BMI may be determined as follows:

$$BMI = \frac{\text{Weight (lb)}}{\text{Height}^2 \text{ (in}^2\text{)}} * 703.0704 \quad \text{Equation (2)}$$

Further, Cholesterol may include low-density lipoprotein (LDL), high-density lipoprotein (HDL), and triglyceride.

In order for the basescore determination module 281 to determine the base diabetes score component of the diabetes risk score, the base diabetes score component may be determined by using engines, such as MEDINDIA, CLINRISK, or AMERICAN DIABETES ASSOCIATION. The base diabetes score component may be adjusted for BMI as follows:

$$\text{baseScore} = \text{baseScore}_{healthy} * \Delta_{BMI} \quad \text{Equation (3)}$$

Figure 22:
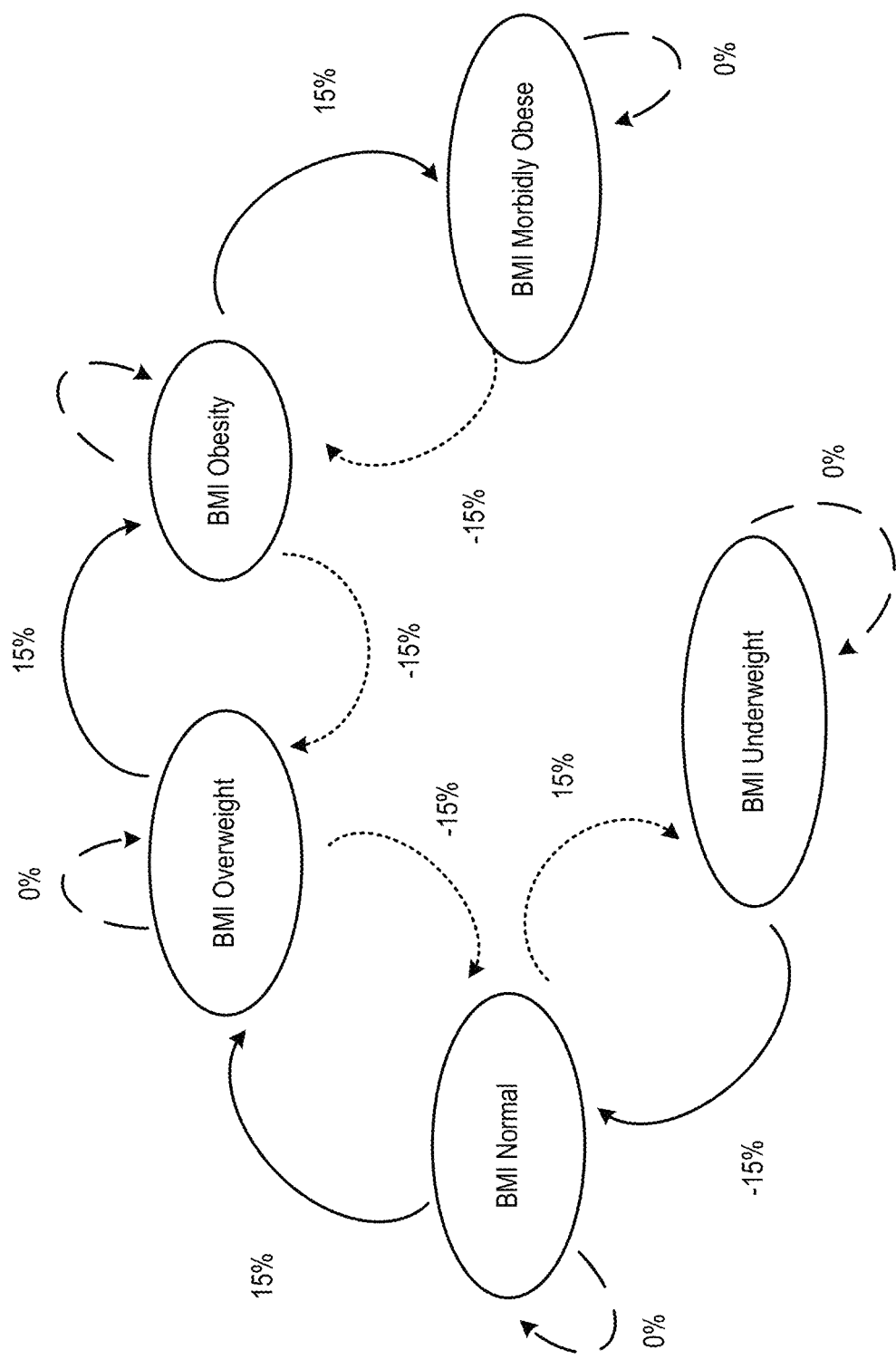
FIG. 22 illustrates a BMI basescore state diagram, according to an example of the present disclosure.
Figure 23:
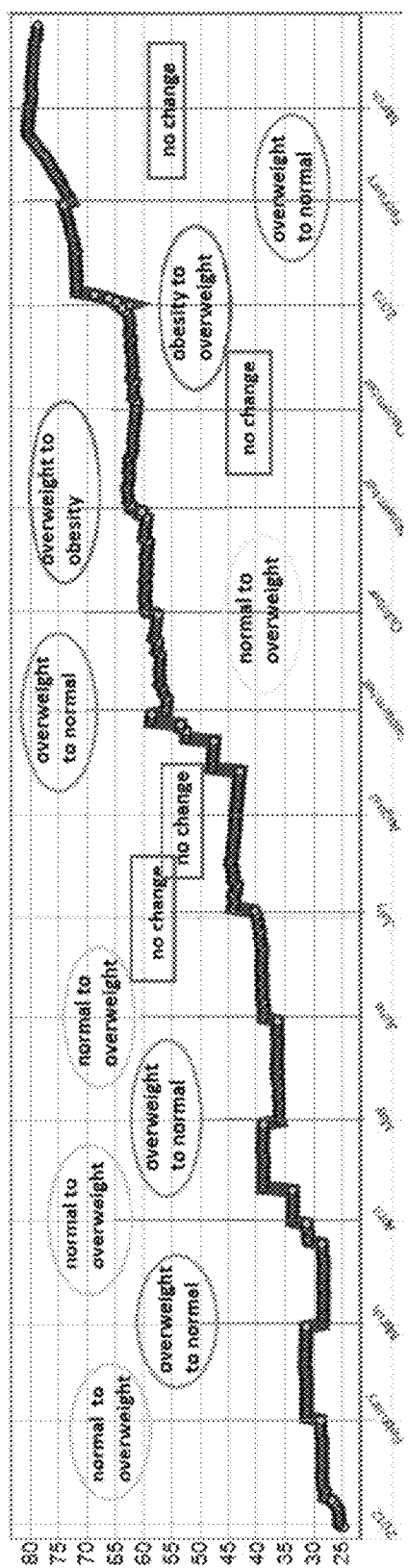
FIG. 23 illustrates a lifeline showing effect of BMI fluctuation, according to an example of the present disclosure.

For example, FIG. 21 illustrates a BMI table, and FIG. 22 illustrates a BMI basescore state diagram for modifying the basescore based on the BMI table values, according to an example of the present disclosure. The BMI table and/or the BMI basescore state diagram of FIGS. 21 and 22, respectively, may be used to adjust the base diabetes score component. For example, compared to a normal BMI, if the patient 102 is overweight, a $\Delta_{BMI}$ of 1.15 (i.e., +15%) may be used to adjust the base diabetes score component. FIG. 23 illustrates a lifeline showing effect of BMI fluctuation, according to an example of the present disclosure. For example, at time $t_0$ (i.e., the beginning of the lifeline of FIG. 23), the patient 102 has an initial BMI score of 23 which implies that the patient falls in the normal range. As the patient's BMI score fluctuates every month, the effect on the diabetes risk score can be seen in the lifeline of FIG. 23.

Figure 24:
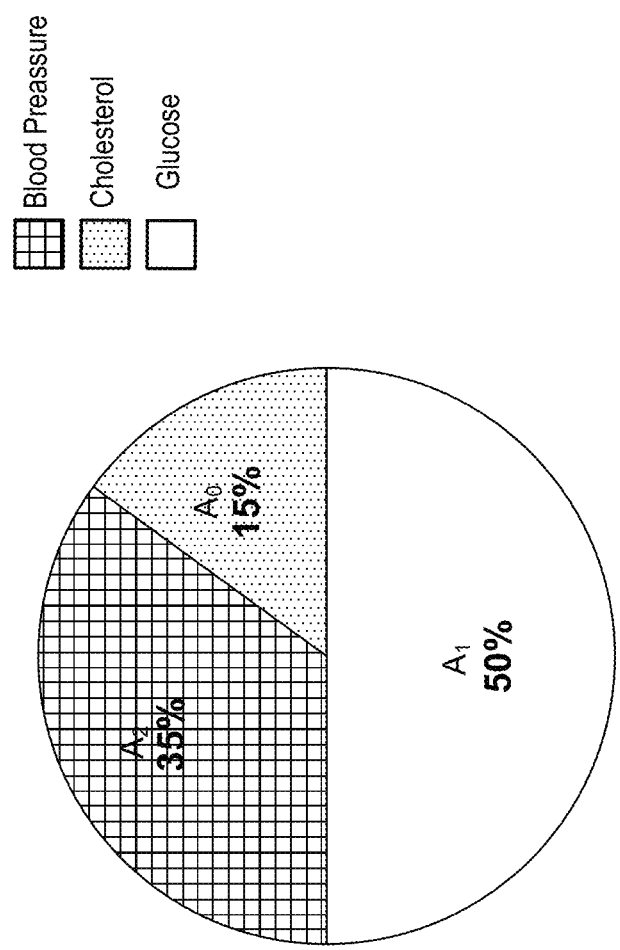
FIG. 24 illustrates distribution of weight for cholesterol, glucose, and blood pressure, according to an example of the present disclosure.

Referring to FIGS. 1, 17, and 24, FIG. 24 illustrates distribution of weight for cholesterol, glucose, and blood pressure, according to an example of the present disclosure. In order for the vitals determination module 282 to determine the vitals component of the diabetes risk score, the vitals component may be determined as follows:

$$\text{vitals} = A_0 * \text{Cholesterol} + A_1 * \text{bloodGlucose} + A_2 * \text{bloodPressure} \quad \text{Equation (4)}$$

For Equation (4), the values of the constants $A_0$, $A_1$, and $A_2$ may be determined such that $\Sigma_{k=0}^{2} A_k = 1$, where $A_k$ is the weight placed on each vitals factor for $k = 0 \ldots 2$. According to an example, the constants $A_0$, $A_1$, and $A_2$ may be set such that $A_0 = 15\%$, $A_1 = 50\%$, and $A_2 = 35\%$, respectively. With respect to cholesterol, cholesterol may be separated into the three groups: good cholesterol (HDL), bad cholesterol (LDL), and triglyceride.

Figure 25:
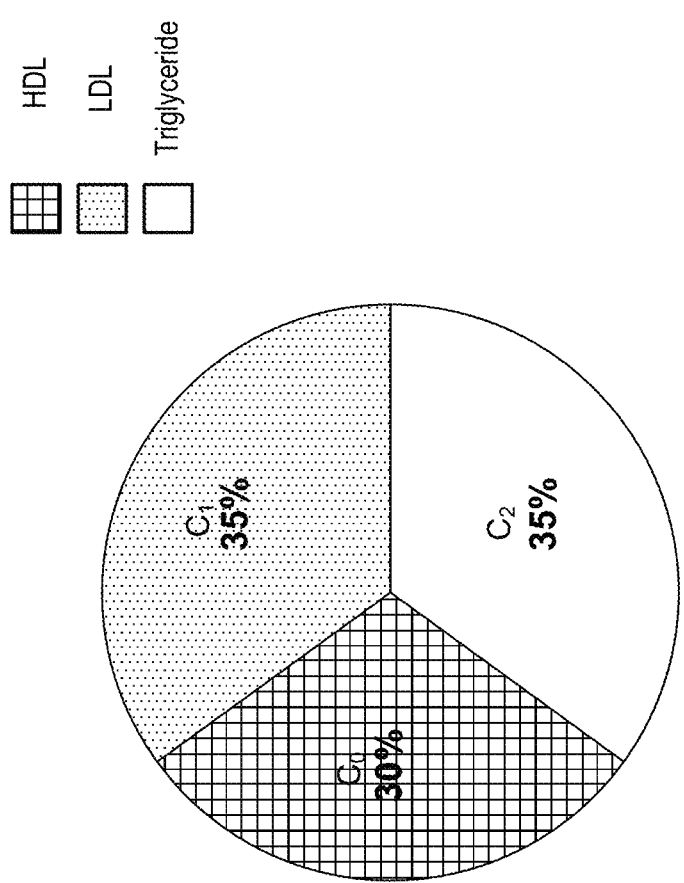
FIG. 25 illustrates distribution of weight for cholesterol attributes, according to an example of the present disclosure.

FIG. 25 illustrates distribution of weight for cholesterol attributes, according to an example of the present disclosure. The cholesterol component of Equation (4) may be determined as follows:

$$\text{Cholesterol} = C_0 * HDL + C_1 * LDL + C_2 * \text{Triglyceride} \quad \text{Equation (5)}$$

For Equation (5), the values of the constants $C_0$, $C_1$, and $C_2$ may be determined such that $\Sigma_{j=0}^{2} C_j = 1$, where $C_j$ is the weight placed on each cholesterol attribute for $j = 0 \ldots 2$. According to an example, the constants $C_0$, $C_1$, and $C_2$ may be set such that $C_0 = 30\%$, $C_1 = 35\%$, and $C_2 = 35\%$. FIG. 26 illustrates patient vitals for cholesterol ranges, according to an example of the present disclosure.

Figure 27:
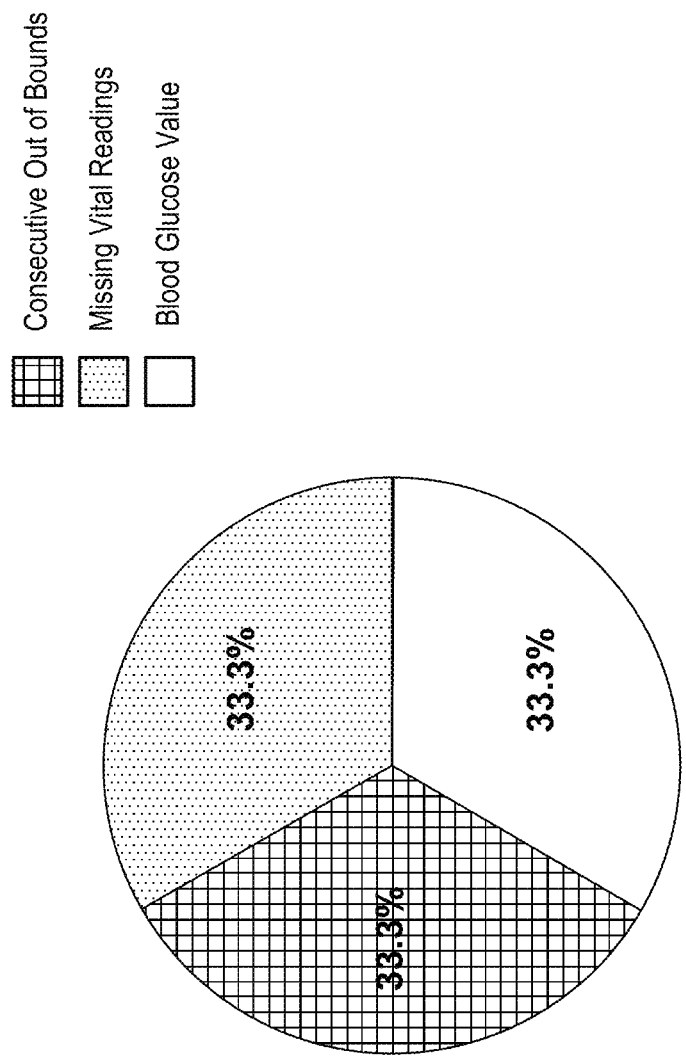
FIG. 27 illustrates patient vitals for blood glucose, according to an example of the present disclosure.

FIG. 27 illustrates patient vitals for blood glucose, according to an example of the present disclosure. The blood glucose component of Equation (4) may be determined as follows:

$$\text{bloodGlucose} = g_{level} * 0.333 + g_{oob} * 0.333 + g_{missing} * 0.333 \quad \text{Equation (6)}$$

Equation (6) takes into consideration the affect glucose readings ($g_{level}$), missed glucose measurements ($g_{missing}$), and out of bounds readings ($g_{oob}$) have on a patient's diabetes risk score for developing diabetes in the future. Under certain circumstances, there is potential for bloodGlucose>1. The variables $g_{oob}$, $g_{level}$, and $g_{missing}$ may be capped to <1. For each factor considered, weights may be allocated such that the weights are evenly distributed. However, the weights may be allocated such that one weight is greater than or less than another weight. Thus, as shown in FIG. 27, the weights may be set at 0.333 (i.e., 33.3%). Determination of $g_{oob}$, $g_{level}$, and $g_{missing}$ is described with reference to FIGS. 29-32.

Figure 28:
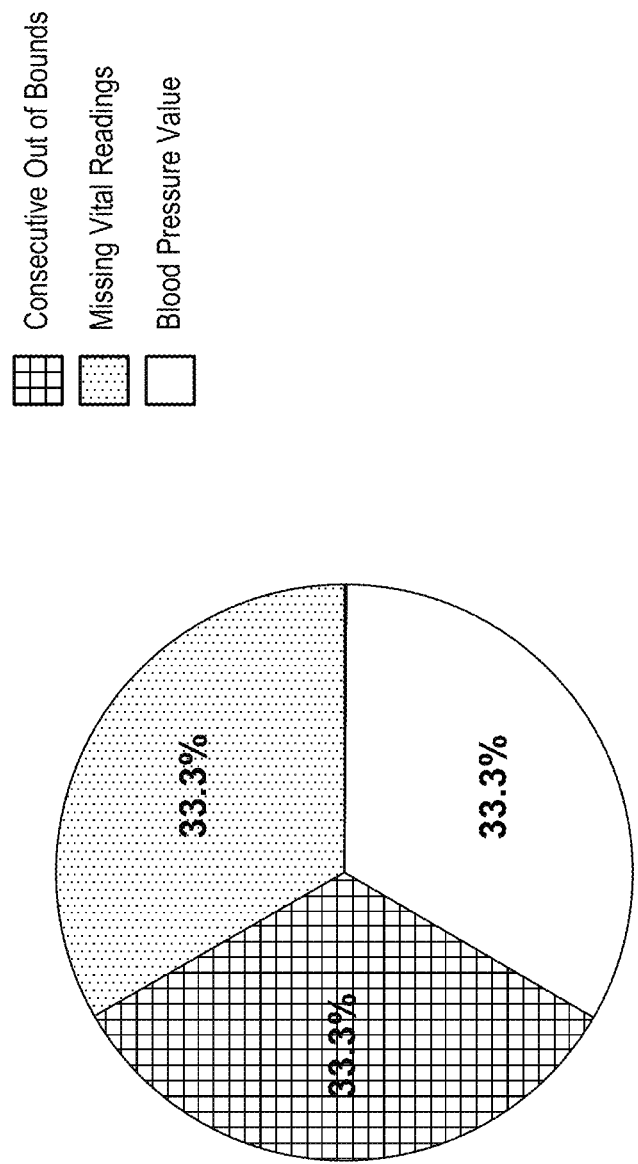
FIG. 28 illustrates patient vitals for blood pressure, according to an example of the present disclosure.

FIG. 28 illustrates patient vitals for blood pressure, according to an example of the present disclosure. The blood pressure component of Equation (4) may be determined as follows:

$$\text{bloodPressure} = b_{systolic}*0.5 + b_{diastolic}*0.5 \quad \text{Equation (7)}$$

$$b_{systolic} = b_{1,level}*0.333 + b_{1,oob}*0.333 + b_{1,missing}*0.333 \quad \text{Equation (8)}$$

$$b_{diastolic} = b_{2,level}*0.333 + b_{2,oob}*0.333 + b_{2,missing}*0.333 \quad \text{Equation (9)}$$

Similar to Blood Glucose calculations, the blood pressure readings ($b_{i,level}$), missed vitals ($b_{i,missing}$), and out of bounds readings ($b_{i,oob}$) may be used to determine the effect on the patient's diabetes risk score. The variables $b_{i,level}$, $b_{i,missing}$, and $b_{i,oob}$ may be capped to <1. For each factor considered, weights may be allocated such that the weights are evenly distributed. However, the weights may be allocated such that one weight is greater than or less than another weight. Thus, as shown in FIG. 28, the weights may be set at 0.333 (i.e., 33.3%, that is evenly distributed between out-of-bounds, missing and actual blood pressure readings).

Figure 29:
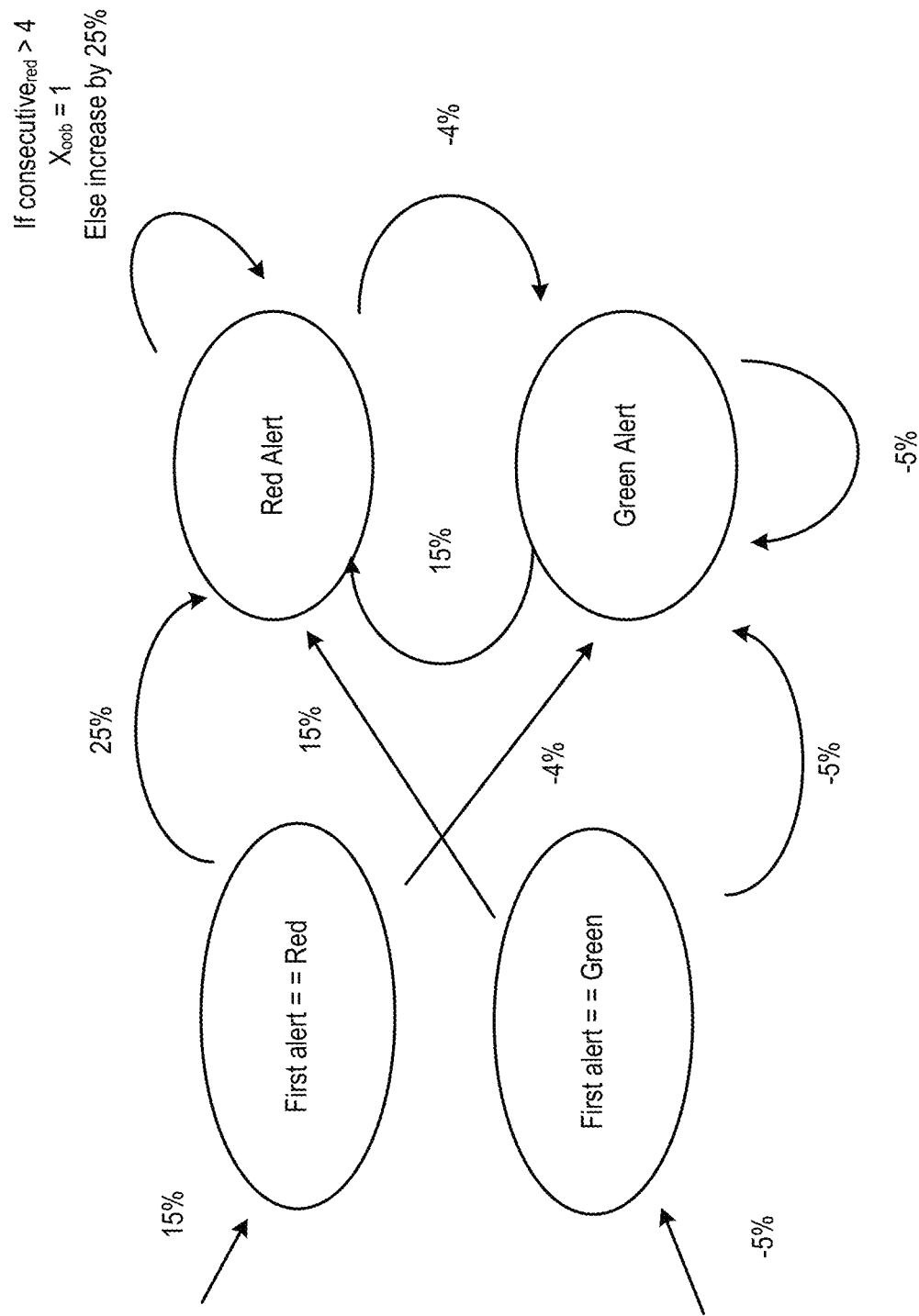
FIG. 29 illustrates a $x_{oob}$ state machine, according to an example of the present disclosure.

Determination of $g_{oob}$, $g_{level}$, and $g_{missing}$, and $b_{i,oob}$, $b_{i,level}$, and $b_{i,missing}$, is described with reference to FIGS. 29-32. The variables $g_{oob}$, $g_{level}$, and $g_{missing}$, and $b_{i,oob}$, $b_{i,level}$, and $b_{i,missing}$ may be generally denoted as $x_{oob}$, $x_{level}$, and $x_{missing}$, respectively. With respect to calculation of $x_{oob}$, FIG. 29 illustrates a $x_{oob}$ state machine, according to an example of the present disclosure. With respect to calculation of $x_{oob}$, the vitals determination module 282 may identify two types of alerts generated for the data. A first alert (e.g., a red alert as shown in FIG. 29) may be identified if there are three consecutive out of bounds values. A second alert (e.g., a green alert as shown in FIG. 29) may be identified if three consecutive in bounds values exist. In determining how alerts play a role in the diabetes risk score, the vitals determination module 282 may consider the following scenarios. The vitals determination module 282 may identify a first occurrence of a red or a green alert, and upon identification, initiate a base diabetes risk score. Alternatively or additionally, the vitals determination module 282 may identify the number of consecutive red alerts that have occurred given that the current alert is red. Alternatively or additionally, the vitals determination module 282 may identify whether or not the previous alert was green given the current alert is red. Alternatively or additionally, the vitals determination module 282 may identify the number of consecutive green alerts that have occurred given that the current alert is green. Alternatively or additionally, the vitals determination module 282 may determine whether or not the previous alert was red given the current alert is green. Alternatively or additionally, the vitals determination module 282 may determine the accumulation of days in which no alerts occur. For each of the foregoing scenarios identified by the vitals determination module 282, each scenario may incur a change in the risk score.

Figure 30:
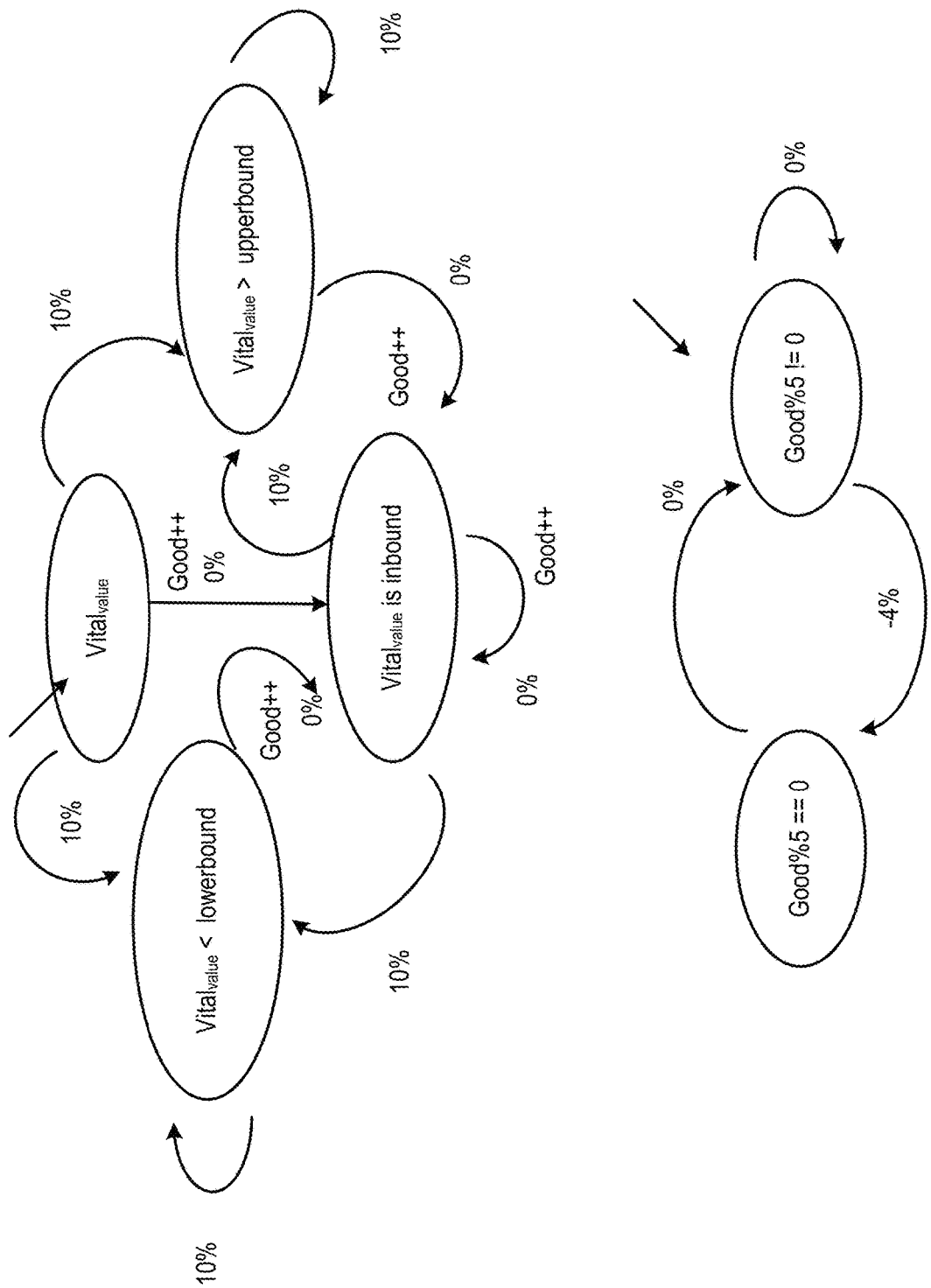
FIG. 30 illustrates a $x_{level}$ state machine, according to an example of the present disclosure.

FIG. 30 illustrates a $x_{level}$ state machine, according to an example of the present disclosure. With respect to calculation of $x_{level}$, the risk associated with the blood glucose levels are based on the provided upper and lower bounds specific to each patient. According to an example, blood glucose levels may be measured three times per day. With respect to $g_{level}$, a $g_{level}$ may be based on a daily average of the blood glucose values taken throughout the day. If the average blood glucose level per day is within a prescribed bounds tailored for a specific patient, then the patient is determined to have met their target blood glucose level and is determined to have a normal blood glucose level, and $g_{level}$ will be 0%. If the patient's average blood glucose level is out of bounds, $g_{level}$ will be 10%. The values for $b_{i,level}$ may be similarly determined.

Figure 31:
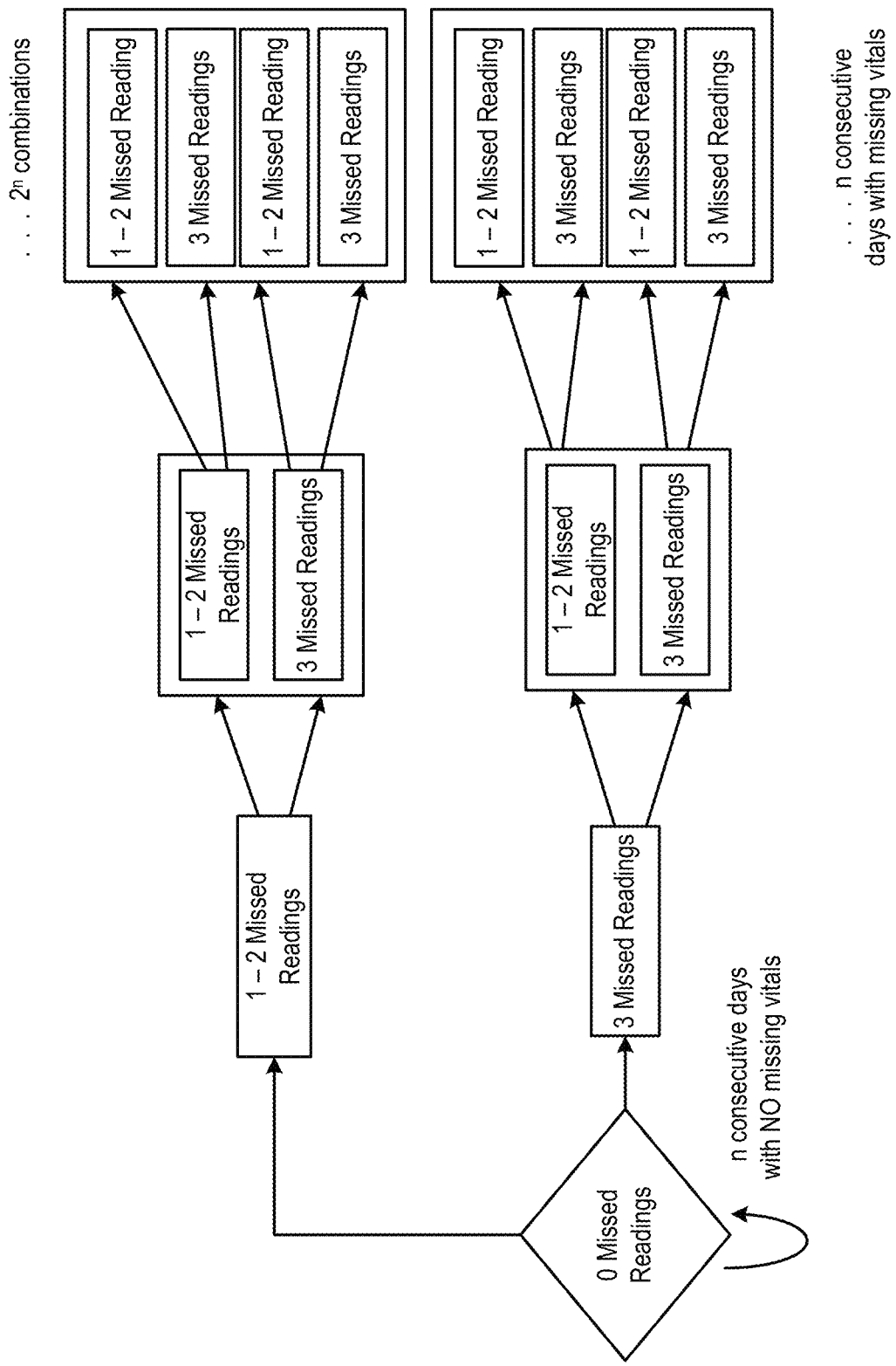
FIG. 31 illustrates calculation of $x_{missing}$, according to an example of the present disclosure.
Figure 32:
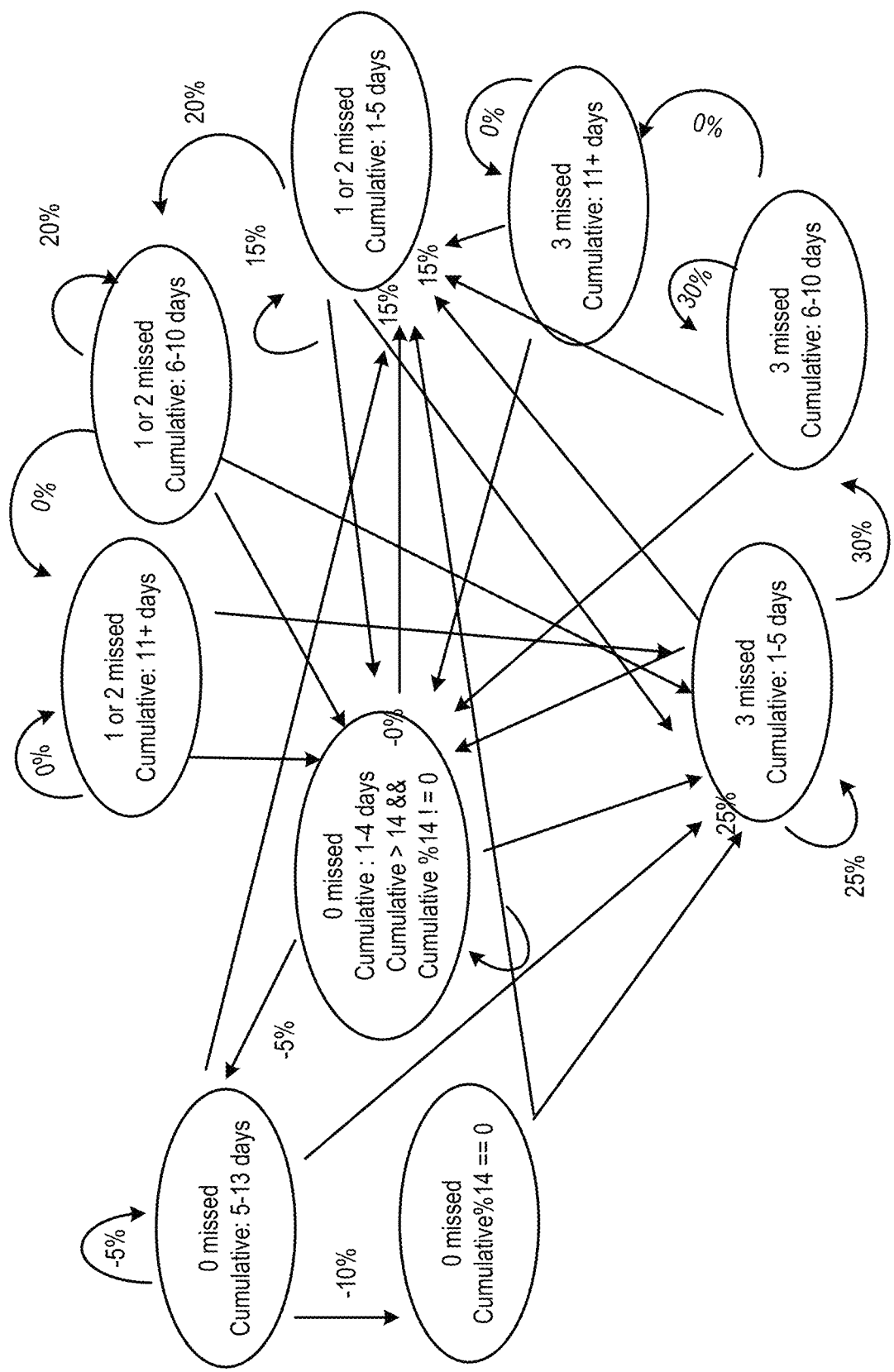
FIG. 32 illustrates a $x_{missing}$ state machine, according to an example of the present disclosure.

FIG. 31 illustrates calculation of $x_{missing}$, and FIG. 32 illustrates a $x_{missing}$ state machine, according to examples of the present disclosure. According to an example, a standard number of vitals measurements are three times per day. For example, occurrences of having 1, 2, or 3 missed vitals readings may affect the diabetes risk score. The vitals determination module 282 may consider the following factors for calculation of $x_{missing}$. The vitals determination module 282 may consider the number of consecutive days where less than three readings per day are taken. Alternatively or additionally, the vitals determination module 282 may consider the number of consecutive days with one or two readings. Alternatively or additionally, the vitals determination module 282 may consider the number of consecutive days with no missing readings regardless of the number of missed readings incurred that day. Alternatively or additionally, the vitals determination module 282 may consider the days with no missing vitals measurements. For each of the foregoing factors identified by the vitals determination module 282, each scenario may incur a change in the diabetes risk score based on the increase or decrease percentage factors illustrated in FIG. 32.

Referring to FIG. 32 that illustrates a $x_{missing}$ state machine, analysis of missing vitals for a case of no missed readings, case A) one to two missed readings, and case B) three missed readings is described. In order to calculate the weight placed on each missed vital at time t (measured in days), the vitals determination module 282 may use historical data. The vitals determination module 282 may analyze three categories of cumulative measurements. The three categories may include a category (i) that includes a number of days with cumulative same case missing vitals (e.g., case A, and case B), a category (ii) that includes a total number of cumulative days with missing vitals regardless of case A or B, and a category (iii) that includes a total number of cumulative days without any missing vitals (e.g., good behavior). When a missing vital occurs, categories (i) and (ii) will apply a cumulative % percent increase on the diabetes risk score. If the patient surpasses 10 cumulative days with missing vital measurements, then the diabetes risk score becomes unaffected. Under this circumstance, the vitals determination module 282 may determine that the patient does not care about monitoring their vitals. Thus missing vitals past the 10 day mark may not affect the diabetes risk score. With respect to category (iii), if the patient has no missed vital readings for 5, 6, and 7-13 consecutive days, their diabetes risk score may decrease variably. For example, the greater the number of consecutive days without missed vital readings, the greater the decrease in the patient's diabetes risk score. Suppose n=number of consecutive days without any missed vital readings, for every n mod 14=0, the patient's risk score may decrease more significantly. With respect to constant decrease in diabetes risk score per consecutive day with no missed vitals, this aspect may not be considered by the vitals determination module 282 so as to provide a threshold in which good behavior/habits in constant vital measurements will help improve a patient's health. The vitals determination module 282 may apply similar logic for a threshold in which constant bad behavior in monitoring a patient's health negatively affects the patient's health.

Referring to FIG. 17, the behavioral determination module 283 may determine a patient behavioral component, for example, related to missed medications, cancelled appointments, missed appointments, and calories (e.g., caloric changes), for determining the diabetes risk score. For example, with respect to missed medications, medication check-ins may be considered under the assumption that the patient needs to check in one time per day. Each prescription may have a different intake frequency but impose a one-time per day check-in rule. In the event multiple drugs are missed on the same day, the diabetes risk score may account for the sum of the number of different medications missed on each missed check-in date. A higher risk score may be associated with the increase of different missed medications for a particular date. The behavioral determination module 283 may also check for consecutively unmissed medications. According to an example, if after a patient misses a medication check-in, the patient has accumulated two weeks of good behavior (e.g., consistently checked in for all their medications), the patient's diabetes risk score may experience a slight decrease. For the diabetes risk score, the variable missedMeds may be capped to <1.

Referring to FIG. 17, the hospital visit determination module 284 may determine a hospital visit component, for example, related to emergency hospital visits, and inpatient hospital visits, for determining the diabetes risk score. For example, each time a patient is admitted to the hospital for "emergency hospital visit" or "inpatient hospital visit", the patient may have a significant increase in their diabetes risk score. For example, the effect of a hospital encounter may increase a patient's risk score by five points. If the patient stays out of the hospital for three weeks after discharge, their diabetes risk score may slowly decrease. A hospital encounter may be given a heavy weight because it implies that the patient is already at a critical stage in their health to require a hospital visit. The hospital visit determination module 284 may also predict a hospital visit such that the diabetes risk score may increase significantly days prior to the actual hospital visit, or the visit may be prevented all together.

Referring to FIG. 17, the unfilled medications determination module 285 may determine an unfilled medications component, for example, related to prescriptions that have not been filled to date, for determining the diabetes risk score. For example, when the patient has an outstanding medication (e.g., an unfilled prescription), the diabetes risk score may increase significantly the day after their fill window. Patients may be given until their fill window to complete the fulfillment of their prescriptions, or otherwise, the diabetes risk score will be increased.

In order to decrease the overall diabetes risk score (i.e., Equation (1)), a patient may maintain their BMI such that the BMI stays within the normal range. Further, the patient may maintain their blood glucose so that the blood glucose stays within a normal range, and monitor and maintain their weight within a normal range. The patient may achieve, for example, 150 minutes per week of moderate-intensity aerobic physical activity, or 90 minutes per week of vigorous-intensity aerobic physical activity, or a combination of the two to improve their health and minimize risks for diabetes and cardiovascular disease. The patient may regulate what they eat and keep up with their doctor's daily recommended nutritional intake. The patient may make behavioral changes and habitually monitor their vitals (e.g., cholesterol, blood pressure). The patient may maintain healthy vital ranges (e.g., cholesterol and blood pressure levels). The patient may make sure that all medications are filled on time, and take their medically prescribed medications. Further, the patient may make it a habitual routine to take care of themselves on a daily basis so as to avoid emergency hospital encounters.

Figure 33:
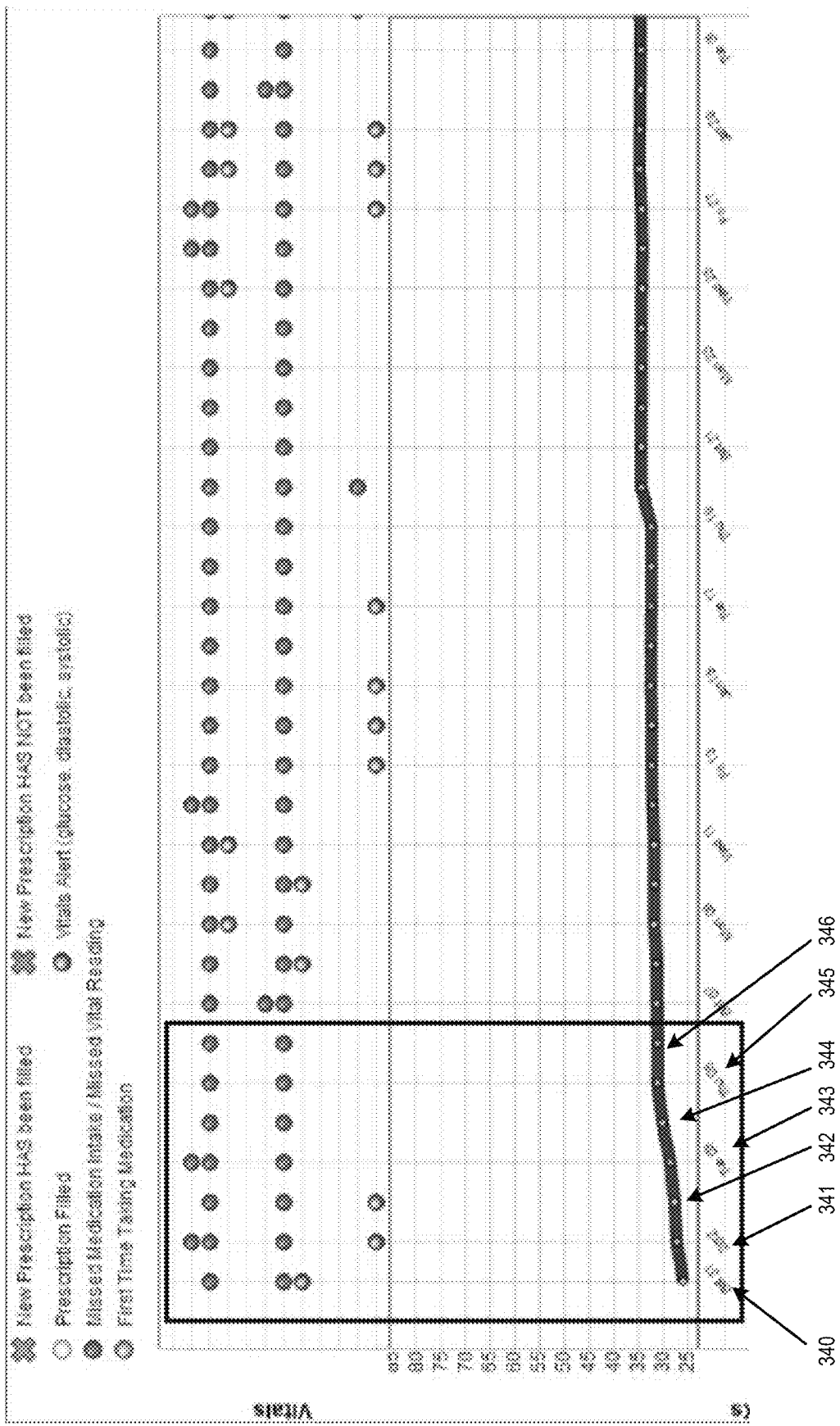
FIG. 33 illustrates a lifeline display for diabetes risk, according to an example of the present disclosure.

FIG. 33 illustrates a lifeline display for diabetes risk, according to an example of the present disclosure. In order to determine the diabetes risk score of Equation (1) and using Equations (2)-(9), if the basescore is determined at 20 for the patient 102, for a day one scenario that includes no glucose alerts and missed glucose readings occurred at day one (i.e., at 340 in FIG. 33), the glucose value will be 0. Further, for the day one scenario where systolic blood pressure experiences an inbound alert and one missed vital reading, diastolic blood pressure experiences one missed vital reading, and there are no occurrences of hospital encounters, unfilled medications, and missed medication check-ins (i.e., 0 values for the associated variables), the diabetes risk score may be determined as follows:

$$bloodGlucose = 0.333*0 + 0.333*0.0 + 0.333*0 = 0$$

$$bDiastolic = 0.333*0 + 0.333*0.0 + 0.333*0.25 = 0.08325$$

$$bSystolic = 0.333*0 + 0.333*0.095 + 0.333*0.25 = 0.114885$$

$$\begin{aligned}\text{Diabetes Risk Score} &= 20 + 70*[0.70*(0.15*0.58175 \\ &+ 0.5*0 + 0.35*(0.5*0.08325 + 0.5*0.114885)) \\ &+ 0.30*0] + 5*0 + 5*0 = 25.975.\end{aligned}$$

Referring to FIG. 33, at day two (i.e., at 341 in FIG. 33), in order to determine the diabetes risk score of Equation (1) and using Equations (2)-(9), for a day two scenario where one out of bounds alert exists for blood glucose readings, this will increase the diabetes risk score associated with bloodGlucose. Further, for the day two scenario where systolic blood pressure has one missed vital reading and diastolic blood pressure has two missed vital readings, based on aggregate historical data, there are a total of two days with one to two missed vital readings for both systolic blood pressure and diastolic blood pressure readings, no alerts have occurred for systolic blood pressure readings since the last green alert (e.g., see FIG. 29) that occurred the day before (this act of health maintenance may contribute to a decrease in the bSystolic risk score), and there are no occurrences of hospital encounters, unfilled medications, and missed medication check-ins (i.e., 0 values for the associated variables), the diabetes risk score may be determined as follows:

$$bloodGlucose = 0.333*0 + 0.333*0.12 + 0.333*0 = 0.03996$$

$$bDiastolic = 0.333*0 + 0.333*0.0 + 0.333*0.337499 = 0.1123875$$

$$bSystolic = 0.333*0 + 0.333*0.094525 + 0.333*0.3374999999 = 0.143864325$$

$$\begin{aligned}\text{Diabetes Risk Score} &= 20 + 70*[0.7*(0.15*0.58175 \\ &+ 0.5*0.03996 + 0.35*(0.5*0.1123875 \\ &+ 0.5*0.143864325)) + 0.3*0] + 5*0 + 5*0 = 27.452\end{aligned}$$

Referring to FIG. 33, at day three (i.e., at 342 in FIG. 33), in order to determine the diabetes risk score of Equation (1) and using Equations (2)-(9), for a day three scenario where one in bound alert exists for blood glucose readings after an out of bounds alert occurred the day before, the inbound alert decreases the bloodglucose risk. Further, for the day three scenario where systolic blood pressure and diastolic blood pressure both have one missed vital reading, based on aggregate historical data, there are a total of three days with one to two missed vital readings for both systolic blood pressure and diastolic blood pressure readings, no alerts have occurred for systolic blood pressure readings since the last green alert (e.g., see FIG. 29) that occurred on day 1 (this act of health maintenance contributes to a decrease in the $b_{1,oob}$ variable of the bSystolic risk score), and there are no occurrences of hospital encounters, unfilled medications, and missed medication check-ins (i.e., 0 values for the associated variables), the diabetes risk score may be determined as follows:

bloodGlucose=0.333*0+0.333*0.1152+
0.333*0=0.0383616 bDiastolic=0.333*0+0.333*0.0+
0.333*0.48937499999=0.1629618 bSystolic=0.333*0+0.333*0.094052375+
0.333*0.48937499999=0.194281

Diabetes Risk Score=20+70*[0.7*(0.15*0.58175+
0.50*0.0383616+0.35*(0.5*0.16296187499+
0.5*0.194281))+0.3*0]+5*0+5*0=28.279

Referring to FIG. 33, at day four (i.e., at 343 in FIG. 33), in order to determine the diabetes risk score of Equation (1) and using Equations (2)-(9), for a day four scenario where neither blood glucose readings nor blood pressure readings experience occurrences of alerts, blood glucose has no missing vitals readings on day four either, and there are no negative marks, the diabetes risk score in the variable bloodGlucose is decreased. Further, for the day four scenario where based on aggregate historical data there are a total of four days with one to two missed vital readings for both systolic blood pressure and diastolic blood pressure readings, continued missed readings will increase the risk score for the variables bDiastolic and bSystolic, no alerts have occurred for systolic blood pressure readings since the last green alert (e.g., see FIG. 29) that occurred on day one (this act of health maintenance contributes to a decrease in the bSystolic risk score), and there are no occurrences of hospital encounters, unfilled medications, and missed medication check-ins (i.e., 0 values for the associated variables), the diabetes risk score may be determined as follows:

bloodGlucose=0.333*0+0.333*0.11462399999+
0.333*0=0.038169792 bDiastolic=0.333*0+0.333*0.0+
0.333*0.7585312499999=0.2525909062499 bSystolic=0.333*0+0.333*0.093582113124999+
0.333*0.7585312499999=0.28375374992

Diabetes Risk Score=20+70*[0.7*(0.15*0.58175+
0.50*0.038169792+0.35*(0.5*0.25259+
0.5*0.283753))+0.3*0]+5*0+5*0=29.81.

Referring to FIG. 33, at day five (i.e., at 344 in FIG. 33), in order to determine the diabetes risk score of Equation (1) and using Equations (2)-(9), for a day five scenario where neither blood glucose readings nor blood pressure readings experience occurrences of alerts, with no negative marks, the diabetes risk score in the variable bloodGlucose is decreased. Further, for the day five scenario where based on aggregate historical data there are a total of five days with one to two missed vital readings for both systolic blood pressure and diastolic blood pressure readings, continued missed readings will increase the risk score for the variables bDiastolic and bSystolic. However, in order to ensure that the probability of all variables is less than 100%, the diabetes risk score values associated with each variable from Equation (1) may be capped at 1. The effect of this cap may be seen when calculating $x_{missing}$ for both the variables bDiastolic and bSystolic. Further, for the day five scenario where no alerts have occurred for systolic blood pressure readings since the last green alert (e.g., see FIG. 29) that occurred on day one, this act of health maintenance contributes to a decrease in the bSystolic risk score. Further, for a scenario where there are no occurrences of hospital encounters, unfilled medications, missed medication check-ins (i.e., 0 values for the associated variables), the diabetes risk score may be determined as follows:

bloodGlucose=0.333*0.0+0.333*0.11405088+
0.333*0=0.03797894304 bDiastolic=0.333*0.0+0.333*0.0+0.333*1=0.333 bSystolic=0.333*0.0+0.333*0.09311420255937498+
0.333*1=0.364007029

Diabetes Risk Score=20+70*[0.7*(0.15*0.58175+
0.50*0.03797894304+0.35*(0.5*0.333+
0.5*0.364007029))+0.3*0]+5*0+5*0=31.183.

Referring to FIG. 33, at day six (i.e., at 345 in FIG. 33), in order to determine the diabetes risk score of Equation (1) and using Equations (2)-(9), if neither blood glucose readings nor blood pressure readings experience occurrences of alerts, with no negative marks, the diabetes risk score in the variable bloodGlucose is decreased. Further, for the day six scenario where based on aggregate historical data there are a total of six days with one to two missed vital readings for both systolic blood pressure and diastolic blood pressure readings, continued missed readings will increase the risk score for the variables bDiastolic and bSystolic. However, in order to ensure that the probability of all variables is less than 100%, the diabetes risk score values associated with each variable from Equation (1) may be capped to 1. The effect of this cap may be seen when calculating $x_{missing}$ for both the variables bDiastolic and bSystolic. Due to the probability cap placed (i.e. already maximizing the variable $x_{missing}$), the overall diabetes risk may decrease due to the fact that the bloodGlucose variable continues to decrease with good adherence to all vital check-ins and vital ranges. For the day six scenario where no alerts have occurred for systolic blood pressure readings since the last green alert (e.g., see FIG. 29) that occurred on day one, this act of health maintenance contributes to a decrease in the bSystolic risk score. Further, for the day six scenario where there are no occurrences of hospital encounters, unfilled medications, missed medication check-ins (i.e., 0 values for the associated variables), the diabetes risk score may be determined as follows:

bloodGlucose=0.333*0.0+0.333*0.1134806256+
0.333*0=0.0377890483248 bDiastolic=0.333*0.0+0.333*0.0+0.333*1=0.333 bSystolic=0.333*0.0+0.333*0.09264863154657811+
0.333*1=0.363851994

Diabetes Risk Score=20+70*[0.7*(0.15*0.58175+
0.50*0.0377890483248+0.35*(0.5*0.333+
0.5*0.363851994))+0.3*0]+5*0+5*0=31.177.

Referring to FIG. 33, at day seven (i.e., at 346 in FIG. 33), in order to determine the diabetes risk score of Equation (1) and using Equations (2)-(9), for a day seven scenario where neither blood glucose readings nor blood pressure readings experience occurrences of alerts, with no negative marks, the risk score in the variable bloodGlucose is decreased. Further, for the day seven scenario where based on aggregate historical data there are a total of seven days with one to two missed vital readings for both systolic blood pressure and diastolic blood pressure readings, continued missed readings will increase the risk score for the variables bDiastolic and bSystolic. However, in order to ensure that the probability of all variables is less than 100%, the diabetes risk score values associated with each variable from Equation (1) may be capped to 1. The effect of this cap may be seen when calculating $x_{missing}$ for both the variables bDiastolic and bSystolic. Due to the probability cap placed (i.e. already maximizing the variable $x_{missing}$), the overall risk may decrease due to the fact that the bloodGlucose variable continues to decrease with good adherence to all vital check-ins and vital ranges. Further, for the day seven scenario where no alerts have been generated for systolic blood pressure readings since the green alert (e.g., see FIG. 29) that occurred on day one, this act of health maintenance contributes to a decrease in the bSystolic risk score. Further, for the day seven scenario where there are no occurrences of hospital encounters, unfilled medications, missed medication check-ins (i.e., 0 values for the associated variables), the diabetes risk score may be determined as follows:

bloodGlucose=0.333*0.0+0.333*0.112913222472+ 0.333*0=0.0376 bDiastolic=0.333*0.0+0.333*0.0+0.333*1=0.333 bSystolic=0.333*0.0+0.333*0.09218538838884523+ 0.333*1=0.3636977343

Diabetes Risk Score=20+70*[0.7*(0.15*0.58175+ 0.50*0.0376+0.35*(0.5*0.333+ 0.5*0.3636977343))+0.3*0]+5*0+5*0=31.171.

Referring to FIG. 33, the diabetes risk score may be similarly calculated for additional days using Equations (1)-(9).

Figure 34:
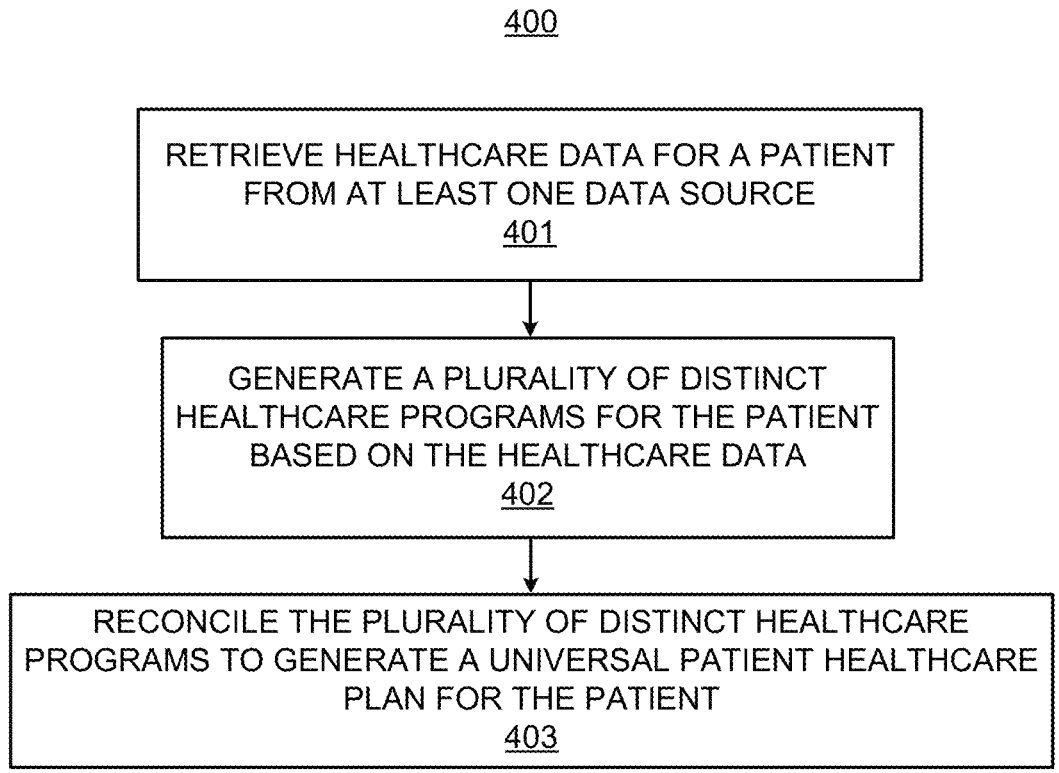
FIG. 34 illustrates a flowchart of a method for collaborative healthcare, according to an example of the present disclosure.

FIG. 34 illustrates a flowchart of a method 400 for collaborative healthcare, corresponding to the example of the collaborative healthcare system 100 whose construction is described in detail above. The method 400 may be implemented on the collaborative healthcare system 100 with reference to FIGS. 1-33 by way of example and not limitation. The method 300 may be practiced in other systems.

Referring to FIG. 34, for the method 300, at block 301, the method may include retrieving healthcare data for a patient from at least one data source. For example, referring to FIG. 1, the system 100 may retrieve and/or transmit healthcare data for the patient 102 from/to at least one data source. For example, the system 100 may receive and/or transmit data to the healthcare provider 103, family and friends 104 of the patient 102, the payer 105, the pharmacy 106, and social networks 107.

At block 302, the method may include generating a plurality of distinct healthcare programs for the patient based on the healthcare data. For example, referring to FIG. 1, the system 100 may generate a plurality of distinct healthcare programs for the patient 102 based on the healthcare data.

At block 303, the method may include reconciling the plurality of distinct healthcare programs to generate a universal patient healthcare plan for the patient. The universal patient healthcare plan may include a universal view of the overall healthcare for the patient and healthcare provider-specific views for the patient. The reconciling may include detecting conflicts for predetermined components of the healthcare programs, and in response to the detection of the conflicts, eliminating errors related to the detected conflicts. For example, referring to FIGS. 1 and 9, the healthcare plan 190 may include healthcare programs 191-193. For example, the healthcare programs 191-193 may be respectively related to heart disease, cancer, and diabetes for the patient 102. Further, referring to FIG. 1, the healthcare plan reconciliation module 101 may detect conflicts for predetermined components of the healthcare programs, and in response to the detection of the conflicts, eliminate errors related to the detected conflicts.

According to a further example, detecting conflicts for predetermined components of the healthcare programs may further include detecting conflicts for patient vitals, patient medications, patient lifestyle, patient appointments, and business rule components of the healthcare programs. For example, referring to FIG. 1, the healthcare plan reconciliation module 101 may detect conflicts, for example, between vitals, medications, lifestyle, appointments, and business rule components of a patient's healthcare programs, for example, for the patient 102.

According to another example, the reconciling may further include determining patient preferences related to the predetermined components, and recommending changes to the healthcare programs based on the patient preferences and the detection of conflicts. For example, recommendations (i.e., suggestions) may be informed based on a patient's preferences. For example, if a patient's profile data indicates that they should lose weight, and they have a preference for weightlifting over cardiovascular exercise, the decision support module 109 may recommend to the healthcare provider that the patient perform, for example, twenty repetitions of three different muscle groups for two sets, three times a week to meet an overall goal of burning 400 calories.

According to another example, recommending changes to the healthcare programs based on the patient preferences and the detection of conflicts may further include recommending changes to the healthcare programs based on social network website data related to behavior of the patient. For example, referring to FIG. 1, the decision support module 109 may operate on data feeds from a patient's personal health records, as well as any third-party data about a patient's behavior (e.g., the sentiment of the patient's TWITTER feeds, which would be an indicator for the patient's mood, or the mention of a jog on the patient's FACEBOOK post).

According to another example, the reconciling may further include providing real-time connection for healthcare providers associated with the healthcare programs to resolve errors related to the detected conflicts. For example, referring to FIG. 1, the healthcare plan reconciliation module 101 may automatically connect healthcare providers associated with conflicting healthcare programs in real-time.

According to another example, the method may further include monitoring the universal patient healthcare plan to detect a health event related to the patient, and in response to the detection of the health event, generating an alert to the patient related to the health event, a workflow change related to a treatment of the patient, a recommendation to a healthcare provider related to the health event, and/or an incentive to the patient related to the health event to facilitate the treatment of the patient. For example, referring to FIGS. 1 and 3, the health event 140 may be used by the event management module 111 to generate alerts 141, workflow changes 142, recommendations 143, and/or offer for incentives 144.

According to a further example, the method may further include monitoring the universal patient healthcare plan to detect a health event related to the patient, and in response to the detection of the health event, scheduling an appointment with a healthcare provider based on the health event. For example, referring to FIGS. 1 and 7, the continuity of healthcare may include use of the workflow automation module 112 to provide, for example, automatic scheduling of appointments with a specialist based on health events.

According to another example, the method may further include displaying changes in a plurality of patient health care aspects on a single display for a predetermined duration for the universal patient healthcare plan for the patient. For example, referring to FIGS. 1 and 18, the visualization system display 300 may be provided on a common horizontal axis that is, for example, a time axis. The different aspects that may influence the patient's health may be displayed using colors and/or symbols along the vertical axis. For example, the vertical axis may include information related to drug and supplement usage at 302, healthcare encounters at 303, vitals at 304, mood at 305, check-ins at 306, etc.

According to a further example, generating the plurality of distinct healthcare programs for the patient based on the healthcare data may further include generating a diabetes risk healthcare program for the patient based on the healthcare data, and determining a diabetes risk score for the diabetes risk healthcare program. For example, referring to FIGS. 1 and 17, generating the plurality of distinct healthcare programs for the patient based on the healthcare data may further include generating a diabetes risk healthcare program for the patient based on the healthcare data, and determining a diabetes risk score by using the diabetes risk score determination module 280 for the diabetes risk healthcare program.

According to another example, determining the diabetes risk score for the diabetes risk healthcare program may further include determining a base diabetes score, a patient vitals component, a patient behavioral component, a hospital visit component, and an unfilled medications component for the diabetes risk score. For example, referring to FIGS. 1 and 17, determining the diabetes risk score for the diabetes risk healthcare program may further include determining a base diabetes score by the basescore determination module 281, a patient vitals component by the vitals determination module 282, a patient behavioral component by the behavioral determination module 283, a hospital visit component by the hospital visit determination module 284, and an unfilled medications component by the unfilled medications determination module 285 for the diabetes risk score.

According to another example, determining the base diabetes score may further include adjusting a base diabetes score for a healthy patient based on a BMI for the patient. For example, referring to Equation (3), the base diabetes score component may be adjusted for BMI.

According to another example, determining the patient vitals component may further include determining cholesterol, blood glucose, and blood pressure sub-components of the patient vitals component, as discussed herein with reference to Equations (4)-(9). The cholesterol sub-component may include HDL, LDL, and triglyceride cholesterol, the blood glucose sub-component may include blood glucose readings, missed blood glucose measurements, and out of bounds blood glucose readings, and the blood pressure sub-component may include blood pressure readings, missed vitals, and out of bounds blood pressure readings.

According to another example, the method may further include generating a first alert based on a number of consecutive blood glucose sub-component out of bounds readings or blood pressure sub-component out of bounds readings being greater than a predetermined threshold, and generating a second alert based on the number of consecutive blood glucose sub-component out of bounds readings or blood pressure sub-component out of bounds readings being less than the predetermined threshold. For example, referring to FIG. 29, with respect to calculation of $X_{oob}$, the vitals determination module 282 may identify two types of alerts generated for the data. A first alert (e.g., a red alert as shown in FIG. 29) may be identified if there are three consecutive out of bounds values. A second alert (e.g., a green alert as shown in FIG. 29) may be identified if three consecutive in bounds values exist.

According to another example, determining the patient behavioral component may further include determining the patient behavioral component based on missed medications, cancelled appointments, missed appointments, and caloric changes for the patient. For example, referring to FIG. 17, the behavioral determination module 283 may determine a patient behavioral component, for example, related to missed medications, cancelled appointments, missed appointments, and calories (e.g., caloric changes), for determining the diabetes risk score.

According to another example, determining the hospital visit component may further include determining the hospital visit component based on emergency hospital visits and inpatient hospital visits for the patient. For example, referring to FIG. 17, the hospital visit determination module 284 may determine a hospital visit component, for example, related to emergency hospital visits, and inpatient hospital visits, for determining the diabetes risk score. For example, each time a patient is admitted to the hospital for "emergency hospital visit" or "inpatient hospital visit", the patient may have a significant increase in their diabetes risk score. For example, the effect of a hospital encounter may increase a patient's risk score by five points. If the patient stays out of the hospital for three weeks after discharge, their diabetes risk score may slowly decrease.

According to another example, determining the unfilled medications component may further include determining the unfilled medications component based on unfilled prescriptions for a predetermined time period for the universal patient healthcare plan for the patient. For example, referring to FIG. 17, the unfilled medications determination module 285 may determine an unfilled medications component, for example, related to prescriptions that have not been filled to date, for determining the diabetes risk score. For example, when the patient has an outstanding medication (e.g., an unfilled prescription), the diabetes risk score may increase significantly the day after their fill window.

FIG. 35 shows a computer system 500 that may be used with the examples described herein. The computer system 500 represents a generic platform that includes components that may be in a server or another computer system. The computer system 500 may be used as a platform for the system 100. The computer system 500 may execute, by a processor or other hardware processing circuit, the methods, functions and other processes described herein. These methods, functions and other processes may be embodied as machine readable instructions stored on computer readable medium, which may be non-transitory, such as hardware storage devices (e.g., RAM (random access memory), ROM (read only memory), EPROM (erasable, programmable ROM), EEPROM (electrically erasable, programmable ROM), hard drives, and flash memory).

The computer system 500 includes a processor 502 that may implement or execute machine readable instructions performing some or all of the methods, functions and other processes described herein. Commands and data from the processor 502 are communicated over a communication bus 504. The computer system 500 also includes a main memory 506, such as a random access memory (RAM), where the machine readable instructions and data for the processor 502 may reside during runtime, and a secondary data storage 508, which may be non-volatile and stores machine readable instructions and data. The memory and data storage are examples of computer readable mediums. The memory 506 may include a collaborative healthcare module 520 (and/or a visualization module) including machine readable instructions residing in the memory 506 during runtime and executed by the processor 502. The module 520 may include the modules of the system 100 described with reference to FIGS. 1-33.

The computer system 500 may include an I/O device 510, such as a keyboard, a mouse, a display, etc. The computer system 500 may include a network interface 512 for connecting to a network. Other known electronic components may be added or substituted in the computer system 500.

What has been described and illustrated herein are examples along with some of their variations. The terms, descriptions and figures used herein are set forth by way of illustration only and are not meant as limitations. Many variations are possible within the spirit and scope of the subject matter, which is intended to be defined by the following claims and their equivalents in which all terms are meant in their broadest reasonable sense unless otherwise indicated.

What is claimed is:

1. A computer implemented method for collaborative healthcare, the method comprising:
    retrieving, for the collaborative healthcare, healthcare data for a patient from a plurality of electronic data sources;
    generating, for the collaborative healthcare, a plurality of distinct healthcare programs including a diabetes risk healthcare program for the patient based on the healthcare data retrieved from the plurality of electronic data sources, wherein generating the plurality of distinct healthcare programs including the diabetes risk healthcare program for the patient based on the healthcare data comprises:
        determining a diabetes risk score for the diabetes risk healthcare program to generate a determined diabetes risk score;
        increasing the determined diabetes risk score based on a number of cumulative days of missed vitals readings being below a specified number of cumulative days for the patient to generate an increased diabetes risk score, wherein the number of cumulative days of missed vitals readings represents a total number of days of missed vitals readings for a duration of days, and wherein the specified number of cumulative days for the patient represents a total number of days for the patient for the duration of days;
        decreasing the increased diabetes risk score based on a number of consecutive days without missed vitals readings for the patient to generate a decreased diabetes risk score, wherein the number of consecutive days without missed vitals readings represents a total number of successive days without missed vitals readings; and
        maintaining, to indicate lack of adherence to the diabetes risk healthcare program, the decreased diabetes risk score based on the number of cumulative days of the missed vitals readings being at or above the specified number of cumulative days for the patient to generate a maintained diabetes risk score;
    reconciling, for the collaborative healthcare, the plurality of distinct healthcare programs including the diabetes risk healthcare program that includes the maintained diabetes risk score to generate a universal patient electronic healthcare plan for the patient, wherein the universal patient electronic healthcare plan includes a universal view of an overall healthcare for the patient and healthcare provider-specific views for the patient that is to be displayed on a computer user interface, and wherein the reconciling comprises:
        detecting conflicts for predetermined components of the healthcare programs by
            analyzing each of the predetermined components of the healthcare programs, and
            determining whether an analyzed predetermined component of the analyzed predetermined components violates a condition specified in other ones of the analyzed predetermined components;
        in response to the detection of the conflicts, eliminating errors related to the detected conflicts in the universal patient electronic healthcare plan by selecting one of the analyzed predetermined components that does not violate the condition specified in the other ones of the analyzed predetermined components to be included in the universal patient electronic healthcare plan; and
        modifying, based on the elimination of errors related to the detected conflicts in the universal patient electronic healthcare plan and elimination of adverse outcomes of taking medications in the universal patient electronic healthcare plan, a type of the medication included in the universal patient electronic healthcare plan;
    determining, for the collaborative healthcare, whether a prescribed medication, which includes the modified type of medication, included in the universal patient electronic healthcare plan has been purchased by the patient;
    based on a determination that the prescribed medication included in the universal patient electronic healthcare plan has not been purchased by the patient, generating, for the collaborative healthcare, a recommendation for another medication for which a cost is lower than a cost of the prescribed medication; and
    generating a display of changes in a plurality of patient health care aspects on a single display for a predetermined duration for the universal patient electronic healthcare plan for the patient by
        analyzing the healthcare data for the patient to identify appointment events, healthcare encounters, vital readings, and medication use taper, and
        generating the display to include, on a common horizontal axis, the identified appointment events, healthcare encounters, vital readings, and medication use taper to display changes in the plurality of patient health care aspects on the single display.

2. The method according to claim 1, wherein detecting conflicts for predetermined components of the healthcare programs further comprises:
    detecting conflicts for patient vitals, patient medications, patient lifestyle, patient appointments, and business rule components of the healthcare programs.

3. The method according to claim 1, wherein the reconciling further comprises:
    determining patient preferences related to the predetermined components; and
    recommending changes to the healthcare programs based on the patient preferences and the detection of conflicts.

4. The method according to claim 1, further comprising:
monitoring the universal patient electronic healthcare plan to detect a health event related to the patient; and
in response to the detection of the health event, generating an incentive to the patient related to the health event to facilitate the treatment of the patient, wherein the incentive is associated with a cost of the treatment of the patient.

5. The method according to claim 1, wherein determining the diabetes risk score for the diabetes risk healthcare program further comprises:
determining a base diabetes score, a patient vitals component, a patient behavioral component, a hospital visit component, and an unfilled medications component for the diabetes risk score.

6. The method according to claim 5, wherein determining the patient vitals component further comprises:
determining cholesterol, blood glucose, and blood pressure sub-components of the patient vitals component, wherein the cholesterol sub-component includes high-density lipoprotein (HDL), low-density lipoprotein (LDL), and triglyceride cholesterol, wherein the blood glucose sub-component includes blood glucose readings, missed blood glucose measurements, and out of bounds blood glucose readings, and wherein the blood pressure sub-component includes blood pressure readings, the missed vitals readings, and out of bounds blood pressure readings.

7. The method according to claim 6, further comprising:
generating a first alert based on a number of consecutive blood glucose sub-component out of bounds readings or blood pressure sub-component out of bounds readings being greater than a predetermined threshold that is greater than one; and
generating a second alert based on the number of consecutive blood glucose sub-component out of bounds readings or blood pressure sub-component out of bounds readings being less than the predetermined threshold.

8. The method according to claim 1, further comprising:
generating an alert based on a number of consecutive health event readings associated with the patient being greater than a predetermined threshold that is greater than one.

9. The method according to claim 1, further comprising:
modifying a rule associated with treatment of the patient based on a number of consecutive health event readings associated with the patient being greater than a predetermined threshold that is greater than one.

10. The method according to claim 1, wherein increasing the determined diabetes risk score based on the number of cumulative days of missed vitals readings being below the specified number of cumulative days for the patient further comprises:
increasing the determined diabetes risk score based on the number of cumulative days of same case missed vitals readings being below the specified number of cumulative days for the patient.

11. The method according to claim 1, wherein increasing the determined diabetes risk score based on the number of cumulative days of missed vitals readings being below the specified number of cumulative days for the patient and decreasing the increased diabetes risk score based on the number of consecutive days without missed vitals readings for the patient further comprises:
increasing the determined diabetes risk score by a corresponding percentage increase based on the number of cumulative days of missed vitals readings being below the specified number of cumulative days for the patient; and
decreasing the increased diabetes risk score by a corresponding percentage decrease based on the number of consecutive days without missed vitals readings for the patient.

12. The method according to claim 1, wherein generating the plurality of distinct healthcare programs for the patient based on the healthcare data further comprises:
increasing the maintained diabetes risk score based on a total number of missed medications determined on a specified date.

13. The method according to claim 1, wherein generating the plurality of distinct healthcare programs for the patient based on the healthcare data further comprises:
increasing the maintained diabetes risk score based on an expected health event related to the patient prior to occurrence of the expected health event.

14. The method according to claim 1, wherein generating the plurality of distinct healthcare programs for the patient based on the healthcare data further comprises:
increasing the maintained diabetes risk score by a weighting factor that is greater than one based on a health event severity related to the patient.

15. A collaborative healthcare system comprising:
a healthcare plan reconciliation module, executed by at least one hardware processor, to:
receive a plurality of distinct healthcare programs for a patient, wherein the plurality of distinct healthcare programs includes a diabetes risk healthcare program for the patient;
increase a diabetes risk score of the diabetes risk healthcare program based on a number of cumulative days of missed vitals readings below a specified number of cumulative days for the patient to generate an increased diabetes risk score, wherein the number of cumulative days of missed vitals readings represents a total number of days of missed vitals readings for a duration of days, and wherein the specified number of cumulative days for the patient represents a total number of days for the patient for the duration of days;
decrease the increased diabetes risk score based on a number of consecutive days without missed vitals readings for the patient to generate an decreased diabetes risk score, wherein the number of consecutive days without missed vitals readings represents a total number of successive days without missed vitals readings;
maintain, to indicate lack of adherence to the diabetes risk healthcare program, the decreased diabetes risk score based on the number of cumulative days of the missed vitals readings being at or above the specified number of cumulative days for the patient; and
reconcile the plurality of distinct healthcare programs including the diabetes risk healthcare program that includes the maintained diabetes risk score to generate a universal patient electronic healthcare plan for the patient, wherein the universal patient electronic healthcare plan includes a universal view of an overall healthcare for the patient and healthcare provider-specific views for the patient, and wherein to reconcile, the healthcare plan reconciliation module is further to:
detect conflicts for predetermined components of the healthcare programs;

in response to the detection of the conflicts, eliminate errors related to the detected conflicts; and modify, based on the elimination of errors related to the detected conflicts and elimination of adverse outcomes of taking medications in the universal patient electronic healthcare plan, a type of the medication included in the universal patient electronic healthcare plan; determine whether a prescribed medication included in the universal patient electronic healthcare plan has been purchased by the patient;

based on a determination that the prescribed medication included in the universal patient electronic healthcare plan has not been purchased by the patient, generate a recommendation for another medication for which a cost is lower than a cost of the prescribed medication; and generate a display of changes in a plurality of patient health care aspects on a single display for a predetermined duration for the universal patient electronic healthcare plan for the patient by analyzing healthcare data associated with the plurality of distinct healthcare programs for the patient to identify appointment events, healthcare encounters, vital readings, and medication use taper, and generating the display to include, on a common horizontal axis, the identified appointment events, healthcare encounters, vital readings, and medication use taper to display changes in the plurality of patient health care aspects on the single display.

16. The collaborative healthcare system according to claim 15, wherein to detect conflicts for predetermined components of the healthcare programs, the healthcare plan reconciliation module is further to:

detect conflicts for patient vitals, patient medications, patient lifestyle, patient appointments, and business rule components of the healthcare programs.

17. The collaborative healthcare system according to claim 15, wherein to reconcile, the healthcare plan reconciliation module is further to:

determine patient preferences related to the predetermined components; and recommend changes to the healthcare programs based on the patient preferences and the detection of conflicts.

18. The system according to claim 15, further comprising:

increasing the maintained diabetes risk score by a weighting factor that is greater than one based on a health event severity related to the patient.

19. A non-transitory computer readable medium having stored thereon a computer executable program to provide collaborative healthcare, the computer executable program when executed causes a computer system to:

receive, by a healthcare plan reconciliation module, a plurality of distinct healthcare programs for a patient, wherein the plurality of distinct healthcare programs includes a diabetes risk healthcare program for the patient;

increase a diabetes risk score of the diabetes risk healthcare program based on a number of cumulative days of missed vitals readings below a specified number of cumulative days for the patient to generate an increased diabetes risk score, wherein the number of cumulative days of missed vitals readings represents a total number of days of missed vitals readings for a duration of days, and wherein the specified number of cumulative days for the patient represents a total number of days for the patient for the duration of days;

decrease the increased diabetes risk score based on a number of consecutive days without missed vitals readings for the patient to generate a decreased diabetes risk score, wherein the number of consecutive days without missed vitals readings represents a total number of successive days without missed vitals readings;

maintain, to indicate lack of adherence to the diabetes risk healthcare program, the decreased diabetes risk score based on the number of cumulative days of the missed vitals readings being at or above the specified number of cumulative days for the patient;

reconcile, by the healthcare plan reconciliation module, the plurality of distinct healthcare programs including the diabetes risk healthcare program that includes the maintained diabetes risk score to generate a universal patient electronic healthcare plan for the patient, wherein the universal patient electronic healthcare plan includes a universal view of an overall healthcare for the patient and healthcare provider-specific views for the patient, and wherein to reconcile, the healthcare plan reconciliation module is further to:

detect conflicts for predetermined components of the healthcare programs;

in response to the detection of the conflicts, eliminate errors related to the detected conflicts; and modify, based on the elimination of errors related to the detected conflicts and elimination of adverse outcomes of taking medications in the universal patient electronic healthcare plan, a type of the medication included in the universal patient electronic healthcare plan;

determine whether a prescribed medication included in the universal patient electronic healthcare plan has been purchased by the patient;

based on a determination that the prescribed medication included in the universal patient electronic healthcare plan has not been purchased by the patient, generate a recommendation for another medication for which a cost is lower than a cost of the prescribed medication; and generate a display of changes in a plurality of patient health care aspects on a single display for a predetermined duration for the universal patient electronic healthcare plan for the patient by analyzing healthcare data associated with the plurality of distinct healthcare programs for the patient to identify appointment events, healthcare encounters, vital readings, and medication use taper, and generating the display to include, on a common horizontal axis, the identified appointment events, healthcare encounters, vital readings, and medication use taper to display changes in the plurality of patient health care aspects on the single display.

20. The non-transitory computer readable medium according to claim 19, the computer executable program when executed further causes the computer system to:

generate an alert based on a number of consecutive health event readings associated with the patient being greater than a predetermined threshold that is greater than one.

* * * * *